(12) United States Patent
Baranov et al.

(10) Patent No.: US 12,013,391 B2
(45) Date of Patent: Jun. 18, 2024

(54) STABILIZED CELL ACQUISITION FOR ELEMENTAL ANALYSIS

(71) Applicant: Fluidigm Canada Inc., Markham (CA)

(72) Inventors: Vladimir Baranov, Richmond Hill (CA); Alexander Loboda, Thornhill (CA); Michael Sullivan, Ontario (CA)

(73) Assignee: STANDARD BIOTOOLS CANADA INC., Markham (CA)

( * ) Notice: Subject to any disclaimer, the term of this patent is extended or adjusted under 35 U.S.C. 154(b) by 1226 days.

(21) Appl. No.: 16/383,241

(22) Filed: Apr. 12, 2019

(65) Prior Publication Data

US 2019/0317082 A1   Oct. 17, 2019

Related U.S. Application Data

(60) Provisional application No. 62/657,332, filed on Apr. 13, 2018.

(51) Int. Cl.
*G01N 33/53* (2006.01)
*G01N 33/58* (2006.01)
*H01J 49/10* (2006.01)

(52) U.S. Cl.
CPC ......... *G01N 33/5306* (2013.01); *G01N 33/58* (2013.01); *H01J 49/105* (2013.01); *G01N 2458/15* (2013.01); *G01N 2560/00* (2013.01)

(58) Field of Classification Search
CPC ...... G01N 1/30; G01N 15/1031; G01N 33/58; G01N 1/44; G01N 1/38; G01N 33/54373; G01N 33/5306; G01N 2015/0065; G01N 2458/15; G01N 2015/1006; G01N 2001/302; G01N 2560/00; H01J 49/105
See application file for complete search history.

(56) References Cited

U.S. PATENT DOCUMENTS

| | | | |
|---|---|---|---|
| 5,478,741 A * | 12/1995 | Maret | C07K 14/445 530/391.1 |
| 5,778,681 A | 7/1998 | Li et al. | |
| 6,936,787 B2 | 8/2005 | Tao et al. | |
| 8,591,630 B2 | 11/2013 | Amirav et al. | |
| 9,012,239 B2 * | 4/2015 | Winnik | C08F 8/14 436/528 |
| 2008/0003616 A1 * | 1/2008 | Winnik | C08F 8/42 435/7.1 |
| 2008/0035844 A1 | 2/2008 | Sakata et al. | |
| 2008/0261321 A1 | 10/2008 | Patton et al. | |
| 2011/0290996 A1 | 12/2011 | Shaw et al. | |
| 2012/0085148 A1 | 4/2012 | Amirav et al. | |
| 2015/0183895 A1 * | 7/2015 | Winnik | G01N 33/532 525/360 |
| 2017/0176422 A1 | 6/2017 | Sanders et al. | |

FOREIGN PATENT DOCUMENTS

| | | |
|---|---|---|
| EP | 3260863 A1 | 12/2017 |
| JP | 2016-061586 A | 4/2016 |
| WO | 2017153992 A1 | 9/2017 |

OTHER PUBLICATIONS

Mavropoulos et al. Simultaneous detection of protein and mRNA in Jurkat and KG-1a cells by mass cytometry. Cytometry Part A 2017, vol. 91A, pp. 1200-1208. (Year: 2017).*
International Application No. PCT/US2019/027306 received an International Search Report and Written Opinion dated Jul. 26, 2019, 17 pages.
European Application No. EP19784699.1 received an Extended European Search Report, dated Mar. 14, 2022, 12 pages.
European Application No. EP19784699.1 , "Partial Supplemental European Search Report", dated Dec. 8, 2021, 13 pages.
Easter, et al., Separation and identification of oligonucleotides by hydrophilic interaction liquid chromatography (HILIC) inductively coupled plasma mass spectrometry (ICPMS), Analyis, vol. 135, No. 10, Oct. 2019, p. 4, third paragraph.
Oxley, et al., "Determination of Urea Nitrate and Guanidine Nitrate Vapor Pressures by Isothermal Thermogravimetry", Propellants, Explosives, Pyrotechnics, Vo. 35, No. 3, Jun. 2010, abstract, p. 6, first paragraph and equation 8.
Rayman, et al., "Interaction of Mg2+ with Peptidoglycan and is Relation to the Prevention of Lysis of a Marine Pseudomonad", Journal of Bacteriology, vol. 122, No. 2, May 1975; abstract; p. 650, col. 1, first paragraph; p. 651, col. 2 sixthe paragraph; p. 657, col. 1, second paragraph; p. 658, col. 2, figure 7 and first paragraph.
Xu, et al., "A Sensitive Atomic Absorption Spectrometric Metalloimmunoassay With Copper Nanoparticles Labeling", Microchemical Journal, vol. 126, May 1, 2016, pp. 1-6; abstract; p. 2, figure 1.
Examination Report for EP 19 784 699.1 dated Aug. 28, 2023, 11 pages.

* cited by examiner

*Primary Examiner* — Shafiqul Haq
(74) *Attorney, Agent, or Firm* — Kilpatrick Townsend & Stockton LLP

(57) ABSTRACT

Analyzing samples injected into an inductively coupled plasma source can be improved by one or more of a stabilizing solution mixable with a sample prior to injection and a heated injector. The stabilizing solution can minimize the difference in osmotic pressure between the solution and the cells with a relatively low amount of dissolved solids (e.g., at or below about 0.2%). The stabilizing solution can contain a salt (e.g., ammonium nitrate) present in concentrations of at least 5 mM. The injector can be heated before and/or during injection. In some cases, heat from adjacent parts can be channeled into the injector to improve heating of the injector. An injector heated to sufficient temperatures can minimize solute buildup and can extend the usable time between cleanings. These improvements can be especially useful in elemental analysis, such as inductively coupled plasma mass spectrometry or inductively coupled plasma optical emission spectrometry.

18 Claims, 15 Drawing Sheets

STABILIZED CELL ACQUISITION FOR ELEMENTAL ANALYSIS

CROSS REFERENCE TO RELATED APPLICATIONS

The present application claims the benefit of U.S. Provisional Application No. 62/657,332 filed Apr. 13, 2018 and entitled "STABILIZED CELL ACQUISITION FOR ELEMENTAL ANALYSIS," which is hereby incorporated by reference in its entirety.

TECHNICAL FIELD

The present disclosure relates to improving signal stability in elemental analysis generally and more specifically to improvements in ionizing a sample in conjunction with elemental analysis.

BACKGROUND

Inductively coupled plasma (ICP) is a plasma source used in various fields, such as elemental analysis. A sample provided to the plasma generated by an ICP source can be ionized and atomized before being analyzed, such as through mass spectrometry (MS) or optical emission spectrometry (OES) (e.g., atomic emission spectroscopy, or AES). ICP sources can also be used for other purposes. Samples generally comprise substances dissolved in solution, such as a suspension of substances in a liquid or solid substances carried within a gas flow.

In an ICP source (e.g., ICP torch), plasma is generated when a flow of gas, such as argon, is ionized in an intense electromagnetic field. When an optimal plasma temperature and energy density is generated, a sample that is introduced through the torch into the plasma can be vaporized, atomized, and ionized. Generally, the conditions to achieve an optimal plasma temperature and energy density are reflected by the argon gas flow rate and the power intensity of the electromagnetic field.

An ICP source can include an induction coil and a set of tubes for supplying the gas and the sample to pass through an area of the torch covered by the induction coil. ICP sources often include an inner tube that acts as an injector to covey the sample, a middle tube for supplying gas to be heated and ionized, and an outer tube for providing tangential flow to help maintain the shape of the plasma and protect the walls of the torch from melting.

In elemental analysis, a sample provided to an ICP source can be ionized and then transferred to an elemental analyzer. The process of storing and then injecting the sample into the ICP source can sometimes damage the sample in a fashion that may degrade stability or resolution of the assay. It can be desirable to provide techniques and materials for improving stability and resolution in ICP-based elemental analysis. Further, traditional ICP-based elemental analyzers are subject to contamination over time, such as build up present on the injector. It can be desirable to provide an ICP-based elemental analyzer or ICP source capable of resisting contamination over time.

In multiplexed elemental analysis of element labeled cells (e.g., mass cytometry), cells are suspended in water to avoid metal or heavy elements that would create background noise during elemental analysis. The absence of solutes also reduces caking onto the wall of the ICP injector, which can clog the fluidics.

SUMMARY

The term embodiment and like terms are intended to refer broadly to all of the subject matter of this disclosure and the claims below. Statements containing these terms should be understood not to limit the subject matter described herein or to limit the meaning or scope of the claims below. Embodiments of the present disclosure covered herein are defined by the claims below, not this summary. This summary is a high-level overview of various aspects of the disclosure and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this disclosure, any or all drawings and each claim.

Embodiments of the present disclosure include a sample, comprising: element-tagged analyte comprising analyte bound to element-tagged affinity reagent, wherein the element-tagged affinity reagent comprises an affinity reagent for binding to the analyte and a metal-binding moiety bound to one or more metal elements; and a stabilizing solution having a total dissolved solids at or below approximately 0.2%, wherein the stabilizing solution contains a salt present in concentrations of at least 5 mM.

In some cases, the salt is a non-metallic salt. In some cases, the salt is devoid of carbon. In some cases, the salt is devoid of metals having an atomic mass unit greater than 80. In some cases, the salt includes nitrogen. In some cases, the salt is ammonium nitrate. In some cases, the salt has a vapor pressure of at least 3 Pa at 100° C. In some cases, the salt has a vapor pressure of at least 130 Pa at 150° C. In some cases, the salt has a vapor pressure of at least 250 Pa at 160° C. In some cases, the salt is ammonium acetate. In some cases, the analyte comprises whole cells. In some cases, the stabilizing solution induces sufficiently low osmotic pressure on a membrane of the analyte to avoid osmotic lysis of the analyte. In some cases, the salt is present in the stabilizing solution in concentrations of at or less than 25 mM. In some cases, the stabilizing solution has a pH of between 5-9. In some cases, the stabilizing solution has a pH of between 6-8. In some cases, the metal-binding moiety includes a polymer linked to the affinity reagent and comprising at least one metal-binding pendant group that comprises at least one metal atom. In some cases, the element-tagged analyte comprises first analyte tagged with a first element tag and second analyte tagged with a second element tag that is distinguishable from the first element tag through elemental analysis. In some cases, the affinity reagent comprises an antibody.

Embodiments of the present disclosure include a sample-making kit, comprising element-tagged affinity reagent comprising an affinity reagent for binding to an analyte and a metal-binding moiety bound to one or more metal elements; and a stabilizing solution having a total dissolved solids at or below approximately 0.2%, wherein the stabilizing solution contains a salt present in concentrations of at least 5 mM.

In some cases, the salt is a non-metallic salt. In some cases, the salt is devoid of carbon. In some cases, the salt is devoid of metals having an atomic mass unit greater than 80. In some cases, the salt includes nitrogen. In some cases, the salt is ammonium nitrate. In some cases, the salt has a vapor pressure of at least 3 Pa at 100° C. In some cases, the salt has a vapor pressure of at least 130 Pa at 150° C. In some cases, the salt has a vapor pressure of at least 250 Pa at 160° C. In some cases, the salt is ammonium acetate. In some cases, the affinity reagent is bindable to surfaces of whole cells. In some cases, the stabilizing solution induces sufficiently low osmotic pressure on membranes of whole cells bound to the affinity reagent to avoid osmotic lysis of the whole cells. In some cases, the salt is present in the stabilizing solution in concentrations of at or less than 25 mM. In some cases, the stabilizing solution has a pH of between 5-9. In some cases, the stabilizing solution has a pH of between 6-8. In some cases, the metal-binding moiety includes a polymer linked to the affinity reagent and comprising at least one metal-binding pendant group that comprises at least one metal atom. In some cases, the element-tagged affinity reagent comprises first affinity reagent tagged with a first element tag and second affinity reagent tagged with a second element tag that is distinguishable from the first element tag through elemental analysis.

Embodiments of the present disclosure include a method, comprising: receiving a sample comprising an element-tagged analyte and a stabilizing solution; transporting the sample towards a plasma of an inductively coupled plasma source in a downstream direction to ionize the sample, wherein transporting the sample comprises passing the sample past an inner wall of an injector; ionizing the sample at the plasma; and performing elemental analysis on the ionized sample to detect elements of the element-tagged analyte.

In some cases, the analyte comprises whole cells, and wherein transporting the sample towards the plasma comprises transporting the whole cells towards the plasma. In some cases, transporting the sample towards the plasma comprises transporting the sample through an injector having an inner diameter of between approximately 0.5 mm and 5 mm. In some cases, receiving the sample further comprises mixing the element-tagged analyte and the stabilizing solution. In some cases, the stabilizing solution includes a salt selected to obtain a salt deposition of less than 2% during a 48 hour sample run. In some cases, the stabilizing solution includes a salt selected to maintain a signal drop percentage during elemental analysis of at or less than 5% during a 48 hour sample run.

Embodiments of the present disclosure include a method, comprising providing element-tagged analyte, wherein the element-tagged analyte comprises a sample containing whole cells labeled with element-tagged affinity reagent, wherein each element-tagged affinity reagent comprises an affinity reagent bound to an analyte of the sample and a metal-binding moiety bound to one or more metal elements; and mixing the element-tagged analyte with a stabilizing solution having a total dissolved solids at or below approximately 0.2%, wherein the stabilizing solution contains a salt present in concentrations of at least 5 mM.

In some cases, the salt is a non-metallic salt. In some cases, the salt is devoid of carbon. In some cases, the salt is devoid of metals having an atomic mass unit greater than 80. In some cases, the salt includes nitrogen. In some cases, the salt is ammonium nitrate. In some cases, the salt has a vapor pressure of at least 3 Pa at 100° C. In some cases, the method further comprises passing the sample acquisition solution through an injector heated to a temperature of at least 100 OC. In some cases, the salt has a vapor pressure of at least 130 Pa at 150° C. In some cases, the method further comprises passing the sample acquisition solution through an injector heated to a temperature of at least 150 OC. In some cases, the salt has a vapor pressure of at least 250 Pa at 160° C. In some cases, the method further comprises passing the sample acquisition solution through an injector heated to a temperature of at least 160° C. In some cases, the salt is ammonium acetate. In some cases, the affinity reagent is bindable to surfaces of the whole cells. In some cases, the stabilizing solution induces sufficiently low osmotic pressure on membranes of whole cells bound to the affinity reagent to avoid osmotic lysis of the whole cells. In some cases, the salt is present in the stabilizing solution in concentrations of at or less than 25 mM. In some cases, the stabilizing solution has a pH of between 5-9. In some cases, the stabilizing solution has a pH of between 6-8. In some cases, the metal-binding moiety includes a polymer linked to the affinity reagent and comprising at least one metal-binding pendant group that comprises at least one metal atom. In some cases, the element-tagged affinity reagent comprises first affinity reagent tagged with a first element tag and second affinity reagent tagged with a second element tag that is distinguishable from the first element tag through elemental analysis. In some cases, the salt is selected to obtain a salt deposition of less than 2% during a 48 hour sample run. In some cases, the stabilizing solution includes a salt selected to maintain a signal drop percentage during elemental analysis of at or less than 5% during a 48 hour sample run Embodiments of the present disclosure include a stabilizing solution mixable with a sample for use in inductively coupled plasma elemental analysis, comprising: solute and solvent, wherein the solute is a salt present in concentrations of at least 5 mM, wherein the solution has a total dissolved solids at or below approximately 0.2%, and wherein the solution is devoid of metals having an atomic mass unit greater than 80.

In some cases, the salt is a non-metallic salt. In some cases, the salt is devoid of carbon. In some cases, the salt includes nitrogen. In some cases, the salt is ammonium nitrate. In some cases, the salt has a vapor pressure of at least 3 Pa at 100° C. In some cases, the salt has a vapor pressure of at least 130 Pa at 150° C. In some cases, the salt has a vapor pressure of at least 250 Pa at 160° C. In some cases, the salt is ammonium acetate. In some cases, the stabilizing solution induces sufficiently low osmotic pressure on a membrane of whole cells of the sample to avoid osmotic lysis of the whole cells. In some cases, the salt is present in the stabilizing solution in concentrations of at or less than 25 mM. In some cases, the stabilizing solution has a pH of between 5-9. In some cases, the stabilizing solution has a pH of between 6-8.

Embodiments of the present disclosure include an apparatus, comprising: an inductively coupled plasma source for generating a plasma; an injector having a sample inlet for receiving a sample comprising an element-tagged analyte, wherein the injector is positioned upstream of the inductively coupled plasma source to supply the sample to the plasma; and a heat source thermally coupled to the injector for heating the injector.

In some cases, the apparatus further comprises a heat transfer device thermally coupled to the injector for conveying heat from the heat source. In some cases, the heat transfer device comprises a metallic jacket surrounding at least a portion of the injector. In some cases, the heat source includes at least a portion of a spray chamber positioned upstream of the injector such that heat from the spray chamber is transferred to the injector through the heat transfer device. In some cases, the heat source includes the plasma. In some cases, the heat source comprises an electrical resistance heat source. In some cases, the apparatus further comprises one or more heat pipes extending along a length of the injector. In some cases, the one or more heat pipes are arranged to conduct thermal energy from a higher temperature portion of the injector towards a lower temperature portion of the injector. In some cases, the apparatus further comprises a mass spectrometer positioned downstream of the inductively coupled plasma source for receiving ions from the inductively coupled plasma source. In some cases, the injector has an inner diameter between approximately 0.5 mm and 5 mm. In some cases, the apparatus further comprises a sample source coupled to the injector for providing the sample and a stabilization solution. In some cases, the heat transfer device is coupled to the injector to heat an inner surface of the injector to a temperature sufficient to vaporize or sublimate solute of the stabilization solution. In some cases, the heat transfer device is coupled to the injector to heat an inner surface of the injector to a temperature of at least 150° C.

Embodiments of the present disclosure include a method of using the apparatus(es) disclosed above, comprising: heating the injector using the heat source; passing a sample through the injector to the plasma; ionizing the sample; and performing elemental analysis on the ionized sample.

In some cases, passing the sample through the injector comprises passing a solution comprising an element-tagged analyte and a stabilizing solution. In some cases, heating the injector includes heating the injector to a temperature suitable to obtain a salt deposition of less than 2% during a 48 hour sample run. In some cases, heating the injector comprises passing electricity through an electrical resistance heat source, wherein the heat source is the electrical resistance heat source. In some cases, heating the injector comprises conducting heat from a higher temperature portion of the injector towards a lower temperature portion of the injector using a heat transfer device. In some cases, heating the injector comprises heating the inner wall to a temperature sufficient to vaporize or sublimate or decompose solute of the stabilizing solution.

Embodiments of the present disclosure include a method, comprising: receiving a sample comprising an element-tagged analyte and a stabilizing solution; transporting the sample towards a plasma of an inductively coupled plasma source in a downstream direction to ionize the sample, wherein transporting the sample comprises passing the sample past an inner wall of an injector; and heating the inner wall of the injector.

In some cases, heating the inner wall of the injector begins prior to transporting the sample towards the plasma. In some cases, heating the inner wall of the injector begins after transporting a first portion of the sample towards the plasma. In some cases, the method further comprises passing the sample through a spray chamber, wherein heating the inner wall of the injector comprises conducting heat through a heat transfer device from the spray chamber. In some cases, heating the inner wall of the injector comprises generating heat at a heat source. In some cases, generating heat at the heat source comprises passing electricity through an electrical resistance heat source. In some cases, heating the inner wall of the injector comprises conducting heat from a higher temperature portion of the injector towards a lower temperature portion of the injector using a heat transfer device. In some cases, heating the inner wall of the injector comprises heating the inner wall to a temperature sufficient to vaporize or sublimate solute of the stabilizing solution. In some cases, heating the inner wall of the injector comprises heating the inner wall to a temperature of at least 150 OC. In some cases, the method further comprises: transporting ions of the ionized sample to a mass spectrometer; and analyzing the ions by the mass spectrometer. In some cases, the analyte comprises whole cells, and wherein transporting the sample towards the plasma comprises transporting the whole cells towards the plasma. In some cases, transporting the sample towards the plasma comprises transporting the sample through an injector having an inner diameter of between approximately 0.5 mm and 5 mm. In some cases, receiving the sample further comprises mixing the element-tagged analyte and the stabilizing solution. In some cases, heating the inner wall of the injector includes heating the inner wall to a temperature suitable to obtain a salt deposition of less than 2% during a 48 hour sample run.

Embodiments of the present disclosure include an apparatus, comprising: an injector positionable upstream of an inductively coupled plasma source and suitable for conveying a sample to a plasma of the inductively coupled plasma source, the injector having a sample inlet for receiving the sample, wherein the sample comprise an element-tagged analyte; and a heat source thermally coupled to the injector for heating the injector.

In some cases, the apparatus further comprises a heat transfer device thermally coupled to the injector for conveying heat from the heat source. In some cases, the heat transfer device comprises a metallic jacket surrounding at least a portion of the injector. In some cases, the heat source includes at least a portion of a spray chamber positioned upstream of the injector such that heat from the spray chamber is transferred to the injector through the heat transfer device. In some cases, the heat source includes the plasma. In some cases, the heat source comprises an electrical resistance heat source. In some cases, the apparatus further comprises one or more heat pipes extending along a length of the injector. In some cases, the one or more heat pipes are arranged to conduct thermal energy from a higher temperature portion of the injector towards a lower temperature portion of the injector. In some cases, the apparatus further comprises a mass spectrometer positionable downstream of the inductively coupled plasma source for receiving ions from the inductively coupled plasma source. In some cases, the injector has an inner diameter between approximately 0.5 mm and 5 mm. In some cases, the apparatus further comprises a sample source coupled to the injector for providing the sample and a stabilization solution. In some cases, the heat transfer device is coupled to the injector to heat an inner surface of the injector to a temperature sufficient to vaporize or sublimate solute of the stabilization solution. In some cases, the heat transfer device is coupled to the injector to heat an inner surface of the injector to a temperature of at least 150° C.

BRIEF DESCRIPTION OF THE DRAWINGS

The specification makes reference to the following appended figures, in which use of like reference numerals in different figures is intended to illustrate like or analogous components.

DETAILED DESCRIPTION

Figure 1:
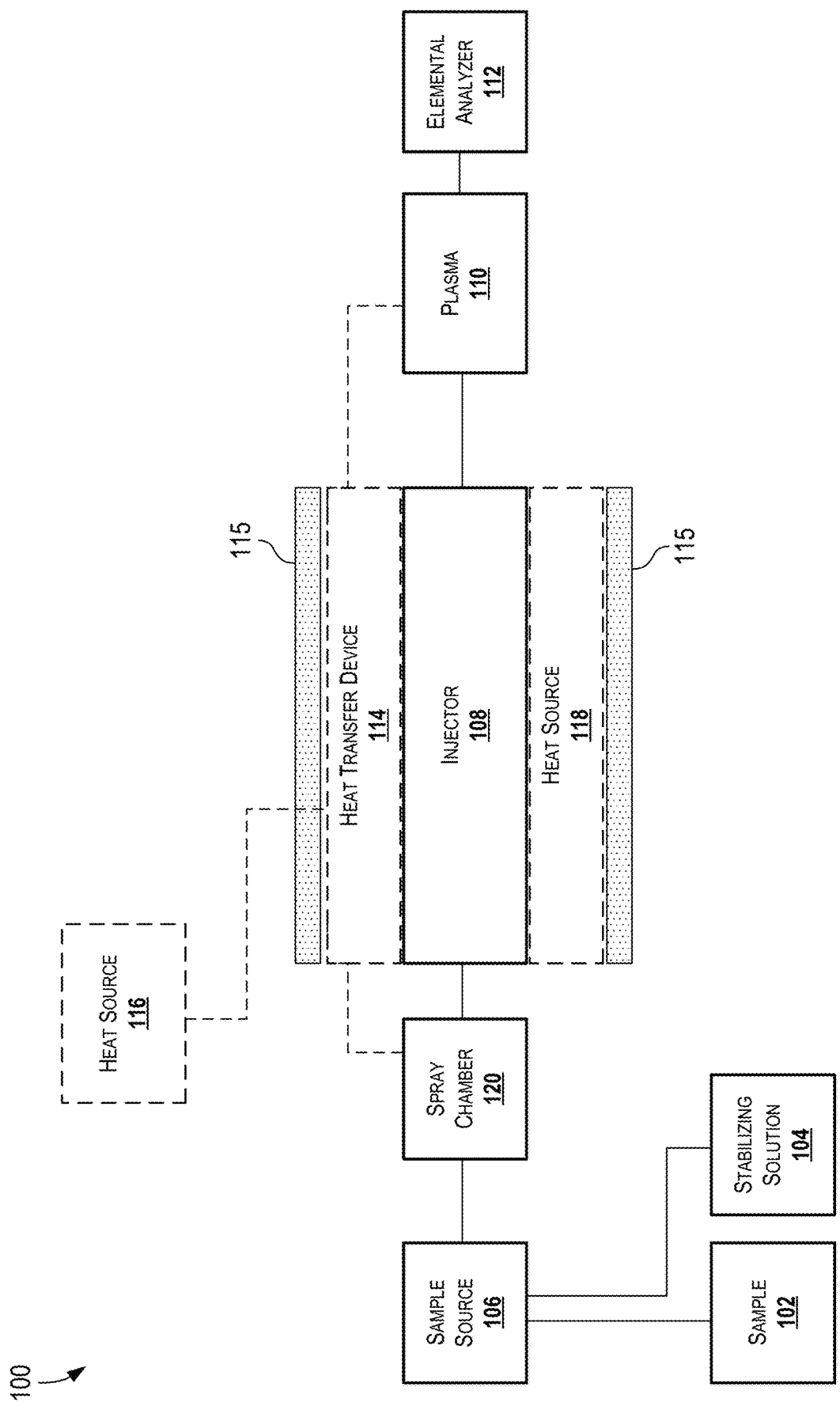
FIG. 1 is a schematic diagram depicting an inductively coupled plasma (ICP) system according to certain aspects of the present disclosure.

Certain aspects and features of the present disclosure relate to improving injection of samples into a plasma source, such as an inductively coupled plasma (ICP) source. Improvements can include one or more of a stabilizing solution mixable with a sample prior to injection and a heated injector. A sample acquisition solution can be prepared by mixing a sample with a stabilizing solution to improve cell stability during injection. The stabilizing solution can minimize the difference in osmotic pressure between the solution and the cells with a relatively low amount of dissolved solids (e.g., at or below about 0.2%). The stabilizing solution can contain a salt (e.g., ammonium nitrate), which can be present in concentrations of at least 5 mM. The injector can be heated before and/or during injection, such as using a heat source or a heat transfer device. In some cases, heat from adjacent parts can be channeled along the injector to improve heating of the injector. An injector heated to sufficient temperatures during use can minimize buildup and extend the usable time between cleanings. These improvements can be especially useful in elemental analysis, such as inductively coupled plasma mass spectrometry (ICP-MS) or inductively coupled plasma optical emission spectrometry (ICP-OES). The improvements can be especially useful with an ICP system operating in suspension mode or solution mode (e.g., with the use of micro-nebulizers).

Certain aspects of the present disclosure are especially useful with elemental analysis. Elemental analysis can refer to techniques for determining the elemental composition (e.g., exact or relative) of a sample, or optionally its isotopic composition (e.g., exact or relative). Non-limiting examples of elemental analysis methods include optical atomic spectroscopy, such as flame atomic absorption, graphite furnace atomic absorption, and inductively coupled plasma atomic emission, which probe the outer electronic structure of atoms; mass spectrometric atomic spectroscopy, such as inductively coupled mass spectrometry, which probes the mass of atoms; and x-ray fluorescence, particle induced x-ray emission, x-ray photoelectron spectroscopy, and Auger electron spectroscopy, which probe the inner electronic structure of atoms.

In some cases, elemental analysis involves use of an inductively coupled plasma mass spectrometer (ICP-MS), which is a sensitive mass spectrometry based elemental analyzer. Different ICP-MS configurations are primarily distinguished by the mass selecting technique employed and can be, for example the quadrupole or time-of-flight (ICP-TOF) or magnetic sector (high resolution ICP-MS). There are many commercially available ICP-MS models having a wide spectrum of configurations, capabilities and modifications.

Elemental analysis can be used to detect element tags associated with an analyte. Element tags, such as element-tagged affinity reagents or element-tagged supports or beads, can be used to label analytes based on the absence or presence of desired biomolecules in the analytes. An element tag, or tag, is a chemical moiety which includes an element, or multiple elements, having one or many isotopes (referred to as tag atoms) attached to a supporting molecular structure, or that is capable of binding said element(s) or isotope(s). The element tag can also comprise the means of attaching the element tag to a molecule of interest or target molecule (for example, an analyte). Different element tags may be distinguished on the basis of the elemental composition of the tags. An element tag can contain many copies of a given isotope and can have a reproducible copy number of each isotope in each tag. Suitable element tags can include polymers (e.g., linear or branched polymers) with metal binding pendant groups, such as metal chelating moieties (e.g., tetraxetan (DOTA) or pentetic acid (DTPA)). Element tags may be a nanoparticle, such metal core encased in a polymer shell. An element tag is functionally distinguishable from other element tags in the same sample because its elemental or isotopic composition is different from that of the other tags. As used herein, the term affinity reagent can refer to a biomolecule capable of tightly binding to a target molecule or analyte. Some non-limiting examples of affinity reagents include aptamers, protein molecules, lectins and polysaccharides. For example, an affinity reagent may be an antibody that recognizes and binds with high affinity to a specific antigen (e.g., on a protein). Streptavidin is a protein molecule that specifically binds biotin and may be considered as another example of an affinity reagent. In some cases, the affinity reagent is a non-oligonucleotide biomolecule.

Non-affinity reagents, such as oligonucleotides used to hybridize to a target oligonucleotide (e.g., DNA, RNA) sequence, may be element tagged and may be used to label target oligonucleotides for elemental analysis. Additional metal containing reagents, including DNA intercalators such as iridium and barcoding reagents, can also be detected by elemental analysis described herein.

To achieve useful results, it can be desirable to select tag atoms that are not otherwise present in the underlying sample or analyte. For example, certain metals, especially lanthanides, are rare in biological samples, and thus may be especially suitable for use in element tags used to assay these biological samples.

The terms biological sample or tissue sample as used herein can refer to a sample obtained from a biological subject, including sample of biological tissue or fluid origin, obtained, reached, or collected in vivo or in situ. A biological sample also includes samples from a region of a biological subject containing precancerous or cancer cells or tissues. Such samples can be, but are not limited to, organs, tissues, fractions and cells isolated from a mammal. Example biological samples include, but are not limited to a cell culture, a cell line, a tissue, an organ, an organelle, a biological fluid, and the like. Example biological samples include, but are not limited to, a skin sample, tissue biopsies, and the like.

As used herein, the term metal can mean an element having one of the following atomic numbers 3, 4, 11-13, 19-33, 37-52, 55-84, 87-102. In some cases, a metal can be a transition element. As used herein, the term transition element can mean an element having one of the following atomic numbers: 21-30, 39-48, 57-80 and 89-92. Transition elements include the rare earth metals, lanthanides and noble metals. As used herein, the term lanthanides can refer to those transition metals with atomic numbers from 57 to 71, including La (lanthanum), Ce (cerium), Pr (praseodymium), Nd (neodymium), Pm (promethium), Sm (samarium), Eu (europium), Gd (gadolinium), Tb (terbium), Dy (dysprosium), Ho (holmium), Er (erbium), Tm (thulium), Yb (ytterbium), Lu (luterium).

Thus, in an example, element-tagged affinity reagent can include a distinguishable element tag (e.g., containing an element or set of elements) bound to an antibody that binds with high affinity to a specific antigen on a protein of interest. After incubating the element-tagged affinity reagent with the analyte and washing away unbound reagent, the analyte sample can be interrogated using elemental analysis to detect the presence of the element tag(s), and thus the presence of the protein of interest can be inferred.

In some cases, the analyte of interest can include biomolecules on or within a cell. In some cases, elemental analysis of whole cells or intact cells can be desirable, such as to determine the presence, quantity, or absence of element tags associated with individual cells of a sample. To achieve reliable per-cell elemental analysis, it can be desirable to deter lysing or other damage to individual cells prior to the cells being ionized at the plasma. In cell acquisition through elemental analysis (e.g., per-cell elemental analysis), damage to cells can result in poor signal stability over the course of a sample.

Certain aspects and features of the present disclosure relate to the use of a stabilizing solution suitable for maintaining high signal stability and/or maintaining individual cells of a sample intact during injection in an ICP system. As used herein, an ICP system can refer to an inductively coupled plasma source (e.g., an ICP torch), and optionally any additional equipment or parts for operating the ICP source, for supplying the sample to the plasma, and/or for conveying the ions for further analysis. The stabilizing solution can be selected to minimize the difference in osmotic pressure between the solution and the cells, which in turn can help keep the cells intact. Alternatively, or in addition, the stabilizing solution may be selected to improve stability of metal chelates of one or more element tags.

However, in some cases, stabilizing solutions can increase the risk of injector clogging, as solutes within the stabilizing solution can condense and accumulate within the injector (e.g., along the inner wall of the injector). In some cases, the development of such buildups and even clogging can be reduced or prevented through the use of a heated injector. In some cases, the combination of a heated injector and a stabilizing solution according to aspects of the present disclosure can improve signal stability when the sample is analyzed using an elemental analyzer.

In some cases, use of a heated injector can permit the use of higher concentrations of stabilizing solution without undesirable negative effects (e.g., without buildups or clogging, without readily perceptible buildups or clogging, or with only minimal buildups or clogging, such as defined by a percentage of the cross section of the injector). In some cases, undesirable effects associated with buildups or clogging can be minimized by using a lower concentration of the stabilizing solution, with or without a heated injector. In some cases, the sample can be at or longer than 48 hours, 36 hours, 32 hours, 28 hours, 24 hours, 20 hours, 16 hours, 12 hours, 8 hours, 4 hours, 2 hours, and/or 1 hour.

As used herein, certain aspects of the present disclosure can prevent buildups or clogging in an injector. The injector can have a nominal cross-sectional area defined as the cross-sectional are of the inner radius of the injector (e.g., $A_{nominal}=\pi r^2$). If buildups or clogging occurs within an injector, the injector can have an effective cross-sectional area that is less than the nominal cross-sectional area based on the extent of the buildups or clogging (e.g., $A_{effective}=\pi r^2 - A_{clog}$, where $A_{clog}$ is the area of the clog or buildup). Certain aspects of the present disclosure can prevent buildups or clogging of an injector during a sample run such that the effective cross-sectional area of the injector remains at or at least approximately 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, and/or 70% of the nominal cross-sectional area of the injector for a 48-hour, 36-hour, 32-hour, 28-hour, 24-hour, 20-hour, 16-hour, 12-hour, 8-hour, 4-hour, and/or 2-hour non-stop (e.g., continuous) operation of the instrument. In some cases, certain aspects of the present disclosure can prevent buildups or clogging of an injector during a sample run such that the effective cross-sectional area of the injector remains at or at least approximately 90% of the nominal cross-sectional area of the injector.

As used herein, certain aspects of the present disclosure can increase the sublimation rate and/or decrease the deposition rate of solution passing through an injector, thus preventing long-term deposition of solute on the inner surface of the injector. An increase in sublimation rate and/or a decrease the deposition rate can correlate to less overall solute buildup on the inner surfaces of the injector during a sample run. Sublimation rate can refer to the rate at which solid solute (e.g., salt of the stabilizing solution) deposited on the inner wall of the injector is transformed into a gas and carried away from the injector. Deposition rate can refer to the rate at which the solute (e.g., salt of the stabilizing solution) is deposited on the injector. Since sublimation is the primary mode by which deposited solute is removed from the injector during operation, the sublimation rate is approximately inversely related to the deposition rate. In some cases, sublimation can be described in terms of a percentage of solute deposited instead of ionized when the solution is passed through an injector and into a plasma. For example, a 5% deposition rate can refer to 5% of the solute in the solution being deposited on the inner walls of the injector. For example, a higher sublimation rate will reduce solute build up on the inner walls of the injector during a sample run. In some cases, approximately 20%, 19%, 18%, 17%, 16%, 15%, 14%, 13%, 12%, 11%, 10%, 9%, 8%, 7%, 6%, 5%, 4.5%, 4%, 3.5%, 3%, 2.5%, 2%, 1.9%, 1.8%, 1.7%, 1.6%, 1.5%, 1.4%, 1.3%, 1.2%, 1.1%, 1%, 0.9%, 0.8%, 0.7%, 0.6%, 0.5%, 0.4%, 0.3%, 0.2%, or 0.1% or 0% of the solute may be deposited on the inner wall of the injector by the end of the sample run. In some cases, the sample run may be at or longer than 48 hours, 36 hours, 32 hours, 28 hours, 24 hours, 20 hours, 16 hours, 12 hours, 8 hours, 4 hours, 2 hours, and/or 1 hour.

Certain stabilizing solutions and optionally heated injectors as described herein can be used to convey a mixture containing a sample (e.g., whole cells) and solute from a stabilizing solution (e.g., salt from a stabilizing solution) through an injector, such as to a plasma. In some cases, the mixture exiting the injector contains at least at or approximately 80%, 81%, 82%, 83%, 84%, 85%, 86%, 87%, 88%, 89%, 90%, 91%, 92%, 93%, 94%, 95%, 95.5%, 96%, 96.5%, 97%, 97.5%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, or 99.9% of the solute that entered the injector. The mixture can be a cell acquisition solution. The cell acquisition solution can be entrained within a gas, such as argon. The cell acquisition solution can be further entrained within a main gas and/or auxiliary gas upon exiting the injector.

In some cases, the sublimation rate may be calculated as the vapor pressure (e.g., expected vapor pressure given the solute and temperature of the injector) of the solute at the injector. Examples of sublimation rates for an example solute are described herein with respect to Table 1.

The choice of stabilizing solution (e.g., type of and concentration of salt in the stabilizing solution) and/or an amount of heating of the injector (e.g., no heating or some heating) can be selected to achieve a desirable sublimation rate and/or a desirable deposition rate.

The choice of stabilizing solution (e.g., type of and concentration of salt in the stabilizing solution) and/or an amount of heating of the injector can be selected to achieve a desirable sublimation rate.

As used herein, certain aspects of the present disclosure can prevent or reduce a percentage of signal drop during the course of a sample run. Signal drop prevention can occur when using a stabilizing solution and/or a heated injector. In some cases, signal drop prevention can be correlated with keeping the injector free from buildups or clogging. In some cases, the percentage of signal drop according to certain aspects of the present disclosure can be at or less than approximately 15%, 14%, 13%, 12%, 11%, 10%, 9%, 8%, 7%, 6%, 5%, 4.5%, 4%, 3.5%, 3%, 2.5%, 2%, 1.5%, 1%, or 0.5%. The signal drop percentage can be calculated over a sample run or a portion of a sample run. In some cases, the signal drop percentage can be calculated over a time period of at or approximately 48 hours, 36 hours, 32 hours, 28 hours, 24 hours, 20 hours, 16 hours, 12 hours, 8 hours, 4 hours, 2 hours, and/or 1 hour. The signal drop percentage can be calculated as the average percentage of the amount the signal deviates from an initial signal measurement or average. The signal may be raw data or normalized. In certain aspects, the signal drop percentage can be calculated as the average signal drop across all mass channels, the largest signal drop percentage, or the signal drop percentage of a mass channel pertaining to a particular analyte of interest.

The heated injector can be heated using any suitable technique. In some cases, the heated injector can be directly heated from a heating device. In some cases, the heated injector can be indirectly heated, such as by channeling heat from other parts of the ICP system or adjacent systems. A heating device (e.g., heat source) can supply heat to the injector. Various types of heating units can be used, such as resistive heating devices, thermoelectric devices, gas-powered heating devices (e.g., direct flame), convection heating devices (e.g., circulating hot fluid, such as air), laser heating devices, or others. In some cases, heat can be applied to a section of the heated injector (e.g., upstream section), allowing additional sections of the heated injector (e.g., downstream section or output tip) to be heated by conduction or convection. For example, heat pipes can be applied to or incorporated within an injector to thermally conduct heat from a first section to a second section. In another example, sufficient heat can be provided to a second section through convection by heating the sample fluid within the injector.

In some cases, the injector can be surrounded completely or partially by a heat transfer device. A heat transfer device can be any suitable device capable of conducting heat into and/or along the injector. Examples of suitable heat transfer device include thermally conductive materials coupled to, disposed upon, and/or incorporated within the injector. For example, an injector may be coated with a metallic sheet. In some cases, a heat transfer device can thermally couple the injector to a heat source (e.g., direct heat source or indirect heat source). For example, a heat transfer device can thermally couple the injector to a spray chamber of an ICP system, allowing heat from the spray chamber to be transferred into the injector. In another example, a heat transfer device can be positioned to conduct heat from the plasma into the injector. In some cases, a non-metallic heat transfer device can be used. As used herein, a heat transfer device thermally coupling the injector to another object or element (e.g., spray chamber or plasma) can include thermally coupling at a heat transfer rate higher than without the heat transfer device. In other words, the heat transfer device can increase the heat transfer rate between the injector and the other object, thus providing for faster heat transfer than if no heat transfer device were used (e.g., if the injector were exposed to standard surrounding air or gases).

In some cases, the heat transfer device can be sized (e.g., sized and/or shaped) to convey sufficient heat from a steady heat source (e.g., a spray chamber held at 200° C.) to increase the temperature of the injector (e.g., the temperature of the inner walls of the injector) to a minimum set temperature (e.g., 160° C.). In such cases, the heat transfer device may result in a temperature gradient along the length of the injector, however the temperature at any point along the inner walls of the injector may maintain at least a minimum set temperature. The minimum set temperature may be at or approximately 160° C. In some cases, the minimum set temperature may be at or at least approximately 100° C., 110° C., 120° C., 130° C., 140° C., 150° C., 160° C., 170° C., 180° C., 190° C., 200° C., 210° C., 220° C., 230° C., 240° C., 250° C., or 260° C. In some cases, multiple heat transfer devices can be used, such as a first heat transfer device coupled to the injector and a second heat transfer device coupled to or positioned adjacent another element of the ICP system.

The heated injector can be especially useful in certain aspects of the present disclosure, such as when the sample is combined with, mixed with, or suspended in a stabilizing solution.

According to certain aspects of the present disclosure, the stabilizing solution can include a salt, such as a non-metallic salt, such as ammonium nitrate. The salt can be selected to achieve a particular vapor pressure at certain temperatures, such as certain temperatures associated with a heated injector. In some cases, ammonium nitrate is the salt used in the stabilizing solution, although other salts can be used. In some cases, chlorine and/or fluorine based solutes can be used and can achieve desirable vapor pressures. Table 1 depicts approximate vapor pressure information associated with ammonium nitrate as a function of temperature, where $$\frac{dm}{dt}$$

is the sublimation rate in micrograms per minute for the given setup.

TABLE 1

Sublimation Rates at Specified Temperatures for Ammonium Nitrate

| Temperature (K) | Vapor Pressure (Pa) | $\frac{dm}{dt}$ (μg/min) |
|---|---|---|
| 376.110 | 4.196 | 2.659 |
| 385.324 | 10.373 | 5.260 |
| 394.738 | 15.890 | 7.254 |
| 398.210 | 19.345 | 8.414 |
| 395.039 | 20.418 | 8.763 |
| 404.931 | 38.447 | 14.119 |
| 404.894 | 51.434 | 17.582 |
| 413.816 | 93.336 | 27.551 |
| 414.119 | 105.908 | 30.304 |
| 415.502 | 137.907 | 36.975 |
| 424.501 | 185.679 | 46.267 |
| 424.653 | 206.878 | 50.195 |
| 423.990 | 208.751 | 50.537 |
| 434.083 | 283.787 | 63.698 |
| 433.756 | 328.103 | 71.059 |

For ammonium nitrate, at 433 Kelvin, or approximately 160° C., the vapor pressure reaches approximately 328 Pa, or approximately 0.3% of atmospheric pressure. The mass flow rate of the evaporated solute can be estimated based on a product of the vapor pressure and the gas flow rate. When the injector flow rate is approximately 0.7 slpm (standard litres per minute) of argon and the sample flow rate is approximately 45 microliters/minute, the amount of ammonium nitrate in the carrier gas (argon) can be calculated to be 0.003% of gaseous volume at 20 mM concentration in the solution. Therefore, at this temperature, ammonium nitrate will be gradually sublimating from the walls of the injector and entering the gas flow. The equilibrium between the gas phase and the solid phase of ammonium nitrate can be shifted by the surface tension in small crystals. Yet, experimentally it has been determined that 160° C. is sufficient to keep surfaces of the injector from "fogging up" with ammonium nitrate deposits, especially under gas flow rates commonly used in inductively coupled plasma sources.

The injector can be heated to a temperature sufficient to facilitate sublimation of the salt of the stabilizing solution. In some cases, the temperature to which the injector is heated can be determined or calculated based on a desired vapor pressure for a particular salt. Techniques for relating temperature to vapor pressure for various salts are known in the art, such as described in Oxley, Jimmie, et al. "Determination of Urea Nitrate and Guanidine Nitrate Vapor Pressures by Isothermal Thermogravimetry." For example, urea nitrate (UN), guanidine nitrate (GN), ammonium nitrate (AN), and tracetone triperoxide (TATP) can have vapor pressure and temperature relationships that approximately follow the following equations, where P is in Pascals and T is in Kelvin, at least in the realm of 300-550 K.

$$\ln(P_{UN}) = 57.377 - \frac{20131}{T}$$

$$\ln(P_{GN}) = 72.189 - \frac{33589}{T}$$

$$\ln(P_{AN}) = 35.141 - \frac{12690}{T}$$

$$\ln(P_{TATP}) = 40.194 - \frac{11026}{T}$$

In some cases, the stabilizing solution can include a salt having a vapor pressure of at least 3 Pa at 100° C., at least 130 Pa at 150° C., and/or at least 250 Pa at 160° C. In some cases, the salt can be selected to have a vapor pressure at 100° C. of at or at least approximately 3 Pa, 8 Pa, 13 Pa, 18 Pa, 23 Pa, 28 Pa, 33 Pa, 38 Pa, 43 Pa, 48 Pa, 53 Pa, 58 Pa, 63 Pa, 68 Pa, 73 Pa, 78 Pa, 83 Pa, 88 Pa, 93 Pa, 98 Pa, 103 Pa, 108 Pa, 113 Pa, 118 Pa, 123 Pa, 128 Pa, 133 Pa, 138 Pa, 143 Pa, 148 Pa, 153 Pa, 158 Pa, 163 Pa, 168 Pa, 173 Pa, 178 Pa, 183 Pa, 188 Pa, 193 Pa, 198 Pa, 203 Pa, 208 Pa, 213 Pa, 218 Pa, 223 Pa, 228 Pa, 233 Pa, 238 Pa, 243 Pa, 248 Pa, 253 Pa, 258 Pa, 263 Pa, 268 Pa, 273 Pa, 278 Pa, 283 Pa, 288 Pa, 293 Pa, 298 Pa, 303 Pa, 308 Pa, 313 Pa, 318 Pa, 323 Pa, 328 Pa, 333 Pa, 338 Pa, 343 Pa, 348 Pa, and/or 350 Pa, although other ranges can be used. The salt can be selected to provide suitable sublimation at the operating temperature of the injector (e.g., either with or without heating) sufficient to avoid deposits on the inner wall of the injector.

In some cases, the stabilizing solution can have a neutral pH or a near-neutral pH (e.g., within 1-2 units of neutral pH). At especially high or low pH, cells of the sample could rupture and/or metals chelated in certain element tags may be disassociated. In some cases, the stabilizing solution can be maintained at a pH between 5-9 (e.g., within 2 units of neutral pH) or 6-8 (e.g., within 1 unit of neutral pH). In some cases, the pH of the stabilizing solution can be at or at least approximately 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, and/or 7, and at or below approximately 9, 8.9, 8.8, 8.7, 8.6, 8.5, 8.4, 8.3, 8.2, 8.1, 8, 7.9, 7.8, 7.7, 7.6, 7.5, 7.4, 7.3, 7.2, 7.1, and/or 7. In some cases, the pH of the stabilizing solution can be within 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, and/or 2 units of neutral pH. The pH of the stabilizing solution can be a function of the solute(s) and their concentration(s). In some cases, the solute(s) and their concentration(s) can be selected to achieve a desirable pH.

The concentration of the salt in the stabilizing solution can be sufficiently high to achieve suitable results (e.g., improved stability), but can be sufficiently low to not produce undesirable background interference. Too-low salt concentration can provide little or no benefit to cell stability and may instead provide some instability. Too-high salt concentration can provide a benefit to cell stability, but with a substantial cost to signal quality due to background interference, especially if the TDS for the salt is greater than certain values (e.g., 0.2%). In some cases, the stabilizing solution can include the salt (e.g., ammonium nitrate) in concentrations of between at or approximately 5-25 mM, such as 6-24 mM, 7-23 mM, 8-22 mM, 9-21 mM, 10-20 mM, 11-19 mM, 12-18 mM, 13-17 mM, 14-16 mM, 5-15 mM, 10-15 mM, 10-25 mM, 15-25 mM, and/or 20-25 mM. In some cases, the stabilizing solution can include the salt in concentrations of at or at least approximately 5 mM, 6 mM, 7 mM, 8 mM, 9 mM, 10 mM, 11 mM, 12 mM, 13 mM, 14 mM, 15 mM, 16 mM, 17 mM, 18 mM, 19 mM, 20 mM, 21 mM, 22 mM, 23 mM, and/or 24 mM. In some cases, the stabilizing solution can include the salt in concentrations of at or less than approximately 25 mM, 24 mM, 23 mM, 22 mM, 21 mM, 20 mM, 19 mM, 18 mM, 17 mM, 16 mM, 15 mM, 14 mM, 13 mM, 12 mM, 11 mM, 10 mM, 9 mM, 8 mM, 7 mM, and/or 6 mM. In some cases, other ranges can be used. In some cases, stabilizing solutions having salt concentrations in the lower portions of the aforementioned ranges (e.g., at or approximately 5-10 mM, 5-9 mM, 5-8 mM, 5-7 mM, 5-6 mM, or 5 mM) can be used without a heated injector. In some cases, stabilizing solutions having salt concentrations in the upper portions of the aforementioned ranges (e.g., at or approximately 10-25, 10-25 mM, 11-25 mM, 12-25 mM, 13-25 mM, 14-25 mM, 15-25 mM, 16-25 mM, 17-25 mM, 18-25 mM, 19-25 mM, 20-25 mM, 21-25 mM, 22-25 mM, 23-25 mM, 24-25 mM, or 25 mM) can be most effective when used with heated injector. In some cases, higher concentrations can be used, especially when used with a heated injector.

In some cases, the stabilizing solution can include a salt that is non-metallic. In some case, the elements of the salt can have an atomic mass unit of 80 or less. In other words, the salt can be devoid of metals or elements having an atomic mass unit greater than 80. In some case, the salt can have an atomic mass unit that is lower than the atomic mass unit of the tag atoms of the element tags. In some cases, the stabilizing solution can be devoid of carbon or substantially free of carbon (e.g., at or less than 1%, 0.95%, 0.9%, 0.85%, 0.8%, 0.75%, 0.7%, 0.65%, 0.6%, 0.55%, 0.5%, 0.45%, 0.4%, 0.35%, 0.3%, 0.25%, 0.2%, 0.15%, 0.1%, 0.05%, and/or 0.01% carbon by weight). As used herein, the term "devoid of" with reference to metals or elements can include none of such metals or elements or a substantially small amount of such metals or elements such that they will be imperceptible or negligible during elemental analysis of a sample containing element-tagged analyte as described herein.

While ammonium nitrate can be an effective salt, other salts can be used. In some cases, the salt can be an ammonium-based molecule. Ammonium-based salts can be highly soluble in water, which can provide beneficial results. In some cases, the salt can be ammonium acetate, ammonium phosphate, ammonium formate, or other such salts. In some cases, the stabilizing solution can include nitrogen or a nitrogen-based molecules. In some cases, the stabilizing solution can include an azide-based salt.

In some cases, certain salts may have elements that degrade overall performance. Examples of degraded performance can include buildup of carbon residue on cones, buildup of salt residue, ion suppression due to high concentrations of easily ionized elements (e.g., Na and K), loss of channels due to ions being present in solution (e.g., ammonium iodide flooding mass channel 127 or ammonium orthomolybdate which contains molybdenum and may flood multiple mass channels between 90-100), and other undesirable effects. In some cases, the choice of salt (e.g., choice of stabilizing solution) can be made to tailor specific properties of an assay. For example, the use of ammonium orthomolybdate may not be problematic if there is no interest in mass channels between 90-100 for the particular element tags being used in the assay.

Cell stability can be desirable in various cytometric techniques, however ICP-based elemental analysis is restricted due to the use of plasma to probe the cells, which is fundamentally limited by the total dissolved solids (TDS). Therefore, traditional solutions used to stabilize cells in other pursuits are ineffective or unavailable for use with elemental analysis, at least ICP-based elemental analysis. For example, in a standard ICP-MS setup, the TDS is kept to at or below 0.2% in order to reduce the effects of interferences. For a 1× phosphate-buffered saline (PBS) solution, the TDS is already 0.8% for the NaCl content alone, which is four times higher than the 0.2% limitation. Therefore, PBS cannot be used in the ICP-MS setup without undesirable interference. In some cases, the stabilizing solution can have a TDS of at or less than 0.2%, 0.19%, 0.18%, 0.17%, 0.16%, 0.15%, 0.14%, 0.13%, 0.12%, 0.11%, 0.1%, 0.09%, 0.08%, 0.07%, 0.06%, 0.05%, 0.04%, 0.03%, 0.02%, and/or 0.01%, although other ranges can be used.

As used herein, an injector of an ICP system can have any suitable inner diameter. In some cases, the injector can have an inner diameter between at or approximately 0.5 mm and 5 mm, such as at or approximately 1-5 mm or 1.5-5 mm. In some cases, the injector can have an inner diameter of at or at least approximately 0.5 mm, 0.6 mm, 0.7 mm, 0.8 mm, 0.9 mm, 1 mm, 1.1 mm, 1.2 mm, 1.3 mm, 1.4 mm, 1.5 mm, 1.6 mm, 1.7 mm, 1.8 mm, 1.9 mm, 2 mm, 2.1 mm, 2.2 mm, 2.3 mm, 2.4 mm, 2.5 mm, 2.6 mm, 2.7 mm, 2.8 mm, 2.9 mm, 3 mm, 3.1 mm, 3.2 mm, 3.3 mm, 3.4 mm, 3.5 mm, 3.6 mm, 3.7 mm, 3.8 mm, 3.9 mm, 4 mm, 4.1 mm, 4.2 mm, 4.3 mm, 4.4 mm, 4.5 mm, 4.6 mm, 4.7 mm, 4.8 mm, or 4.9 mm. In some cases, the injector can have an inner diameter of at or less than approximately 5 mm, 4.9 mm, 4.8 mm, 4.7 mm, 4.6 mm, 4.5 mm, 4.4 mm, 4.3 mm, 4.2 mm, 4.1 mm, 4 mm, 3.9 mm, 3.8 mm, 3.7 mm, 3.6 mm, 3.5 mm, 3.4 mm, 3.3 mm, 3.2 mm, 3.1 mm, 3 mm, 2.9 mm, 2.8 mm, 2.7 mm, 2.6 mm, 2.5 mm, 2.4 mm, 2.3 mm, 2.2 mm, 2.1 mm, 2 mm, 1.9 mm, 1.8 mm, 1.7 mm, 1.6 mm, 1.5 mm, 1.4 mm, 1.3 mm, 1.2 mm, 1.1 mm, 1 mm, 0.9 mm, 0.8 mm, 0.7 mm, or 0.6 mm.

In some cases, the use of a heated injector can also prevent water droplets from forming or collected on the injector. At room temperature, the collection—or fogging—of water droplets on an injector can become a problem, especially at higher liquid flow rates (e.g., 60 μL/min) and relatively low gas (e.g., argon) flow rates (e.g., ~0.7 sLpm). Fogging and droplets on the injector can result in signal instability and, in some cases, even occasional loss of plasma in the inductively coupled plasma source. If the plasma is lost, portions of the sample being examined may not be properly ionized, and thus may not be detected. In some cases, heating the injector can reduce or minimize the forming or collecting of water droplets on the injector, which can improve signal stability and plasma reliability.

These illustrative examples are given to introduce the reader to the general subject matter discussed here and are not intended to limit the scope of the disclosed concepts. The following sections describe various additional features and examples with reference to the drawings in which like numerals indicate like elements, and directional descriptions are used to describe the illustrative embodiments but, like the illustrative embodiments, should not be used to limit the present disclosure. The elements included in the illustrations herein may not be drawn to scale.

FIG. 1 is a schematic diagram depicting an inductively coupled plasma (ICP) system 100 according to certain aspects of the present disclosure. The ICP system 100 can include an injector 108 for conveying a sample (e.g., a sample solution or cell acquisition solution) to plasma 110. The plasma 110 can be a ball, toroidal cylinder, or other shape of plasma generated, for example, by exciting a source gas using electromagnetic induction. It will be appreciated that certain aspects of the present disclosure, such as the stabilizing solution and/or heated injector, can be used beneficially in association with other techniques for plasma generation. Certain aspects of a standard ICP system 100 are not shown in FIG. 1 for illustrative purposes, such as gas flow tubes, induction coils, and sample cones.

A sample 102 can include intact cells (e.g., whole cells) labeled with element tags. A stabilizing solution 104 can be provided as disclosed herein. The stabilizing solution 104 can include a salt as described herein, such as ammonium nitrate in concentrations of 15 mM. The sample 102 and stabilizing solution 104 can be separate or pre-mixed. When mixed, the sample 102 and the stabilizing solution 104 can be considered a "sample solution" or a "cell acquisition solution." The sample 102 and stabilizing solution 104 can be provided to the sample source 106 separately or mixed as a cell acquisition solution. The sample source 106 can be any vessel suitable for storing the sample 102 (e.g., the cell acquisition solution) before being introduced into the injector 108. In some cases, the sample source 106 can be a vial, a syringe, a beaker, a length of tubing, or any other container.

The injector 108 can receive the cell acquisition solution from the sample source 106. In some cases, the cell acquisition solution can be passed through a spray chamber 120, such as to aerosolize the cell acquisition solution, prior to entry into the injector 108. The injector 108 can be a length of tubing of any suitable material, such as quartz. The injector 108 can be any suitable shape or profile, such as cylindrical. The injector 108 can direct the cell acquisition solution into the plasma 110 to ionize the sample 102. In some cases, ionizing the sample 102 can result in ions (e.g., a set of ions or an ion beam), which can be directed towards an elemental analyzer 112 (e.g., a mass spectrometer) for further analysis. In some cases, ionizing the sample 102 can result in optical emissions, which can be directed towards and/or sensed by an elemental analyzer 112 (e.g., an optical emission spectrometer).

In some optional cases, a heat source 118 can be coupled to (e.g., physically), disposed around, and/or adjacent to the injector 108. The heat source 118 can be thermally coupled to the injector 108. For example, heat source 118 can be a resistive heater in the form of a metal coil wrapped around the injector 108. Other heat sources 118 can be used. The heat source 118 can extend for the full length of the injector 108 or for less than the full length of the injector 108. The heat source 118 can generate heat, such as using electrical, magnetic, motive, or other energy.

In some optional cases, a heat transfer device 114 can be coupled to (e.g., physically), disposed around, and/or adjacent to the injector 108. The heat transfer device 114 can be thermally coupled to the injector 108. The heat transfer device 114 can be any suitable device or material capable of conveying heat into and/or along the injector 108. For example, the heat transfer device 114 can convey heat from one section of the injector 108 to another section of the injector 108. In another example, the heat transfer device 114 can convey heat from another object, such as a heat source 116, into the injector 108. Heat transfer device 114 can extend for the full length of the injector 108 or for less than the full length of the injector 108. In some cases, an injector 108 can include a heat source 118 and a heat transfer device 114. In some cases, a heat transfer device 114 can be incorporated into the injector 108, such as in the form of heat pipes integrated into or coupled to the body of the injector 108 (e.g., integrated into channels in a quartz tube or adhered to the surface of the quartz tube using thermal paste).

Heat source 116 can be any suitable heat source thermally couplable to the heat transfer device 114. Examples of suitable heat sources 116 can include resistive heating devices, thermoelectric devices, gas-powered heating devices (e.g., direct flame), convection heating devices (e.g., circulating hot fluid, such as air), laser heating devices, or others.

In some optional cases, one or more heat transfer devices 114 can thermally couple the injector 108 to other elements of the ICP system 100 or nearby systems, such as a spray chamber 120 or the plasma 120, although other sources can be used. In some cases, these elements that are thermally coupled to the injector 108 can be considered heat sources. When thermally coupled to the spray chamber 120, the heat transfer device 114 can convey thermal energy from the spray chamber 120, which can be held at a constant temperature (e.g., 200° C.), to the injector 108 at a suitable rate to ensure the injector 108 remains at temperatures of at least a minimum set temperature (e.g., 160° C.). When thermally coupled to the plasma 110, the heat transfer device 114 may receive heat from the plasma 110 indirectly (e.g., through convection due to heating of nearby gasses or through the radiative heat) and convey the heat to the injector 108 at a rate suitable to ensure the injector 108 remains at temperatures of at least a minimum set temperature (e.g., 160° C.). In some cases, achieving a suitable rate of heat transfer in the heat transfer device 114 can include providing the heat transfer device 114 in a suitable size and/or shape capable of achieving the desired heat transfer rate. In some cases, the heat transfer device 114 can include thermal conduction arrestors to suitably slow the transfer of heat to a desired rate. Thermal conduction arrestors can include gaps in the material of the heat transfer device 114, which can be filled with materials more thermally insulating than the heat transfer device 114 itself, such as flowing carrier gas or ceramic materials.

In some cases, the injector 108 of ICP system 100 is unheated by any heat source 118 or heat transfer device 114. In such cases, the stabilizing solution 104 may include a salt at suitably low concentrations or a salt with sufficiently high vapor pressure at injector temperature to avoid the buildup of residue within the injector 108.

In some cases, the injector 108 of ICP system 100 can be heated, such as through a heat source 118 or heat transfer device 114, and can be provided with a sample 102 without a stabilizing solution 104. In such cases, heating of the injector 108 can provide certain benefits, such as reducing possible buildup of water/solvent droplets or buildup of a residue on the injector 108, without the accompanying benefits of the stabilizing solution 104.

In some cases, a thermal insulation layer 115 can be provided around some or all of the injector 108. The thermal insulation layer 115 can be coupled to or positioned directly around the injector 108, or may be coupled to or positioned around the heat transfer device 114 and/or the heat source 118. The thermal insulation layer 115 can retain heat within the injector 108 by inhibiting radial heat dissipation. The thermal insulation layer 115 can facilitate maintaining a constant injector temperature throughout the injector 108. In some cases, the thermal insulation layer 115 can extend fully around the injector 108, although that need not always be the case. The thermal insulation layer 115 can be formed of any suitable insulating material, such as fiberglass, para-aramid fibers, or aerogel. In some cases, the thermal insulation layer 115 can be an air gap or a vacuum gap. In some cases, the thermal insulation layer may be a solid. In some cases, the thermal insulation layer 115 can be any suitable insulating material that inhibits radial heat dissipation from the injector 108 more than is done by the moving, surrounding supply gas (e.g., argon) to the plasma generator. In some cases, surrounding supply gas (e.g., argon) can be used as a thermal insulation layer 115, such as in cases where the amount of gas (e.g., radial thickness of the volume of gas surrounding an injector) is specifically tailored to achieve a particular desired amount of thermal insulation, such as more than in a traditional injector arrangement.

Figure 2:
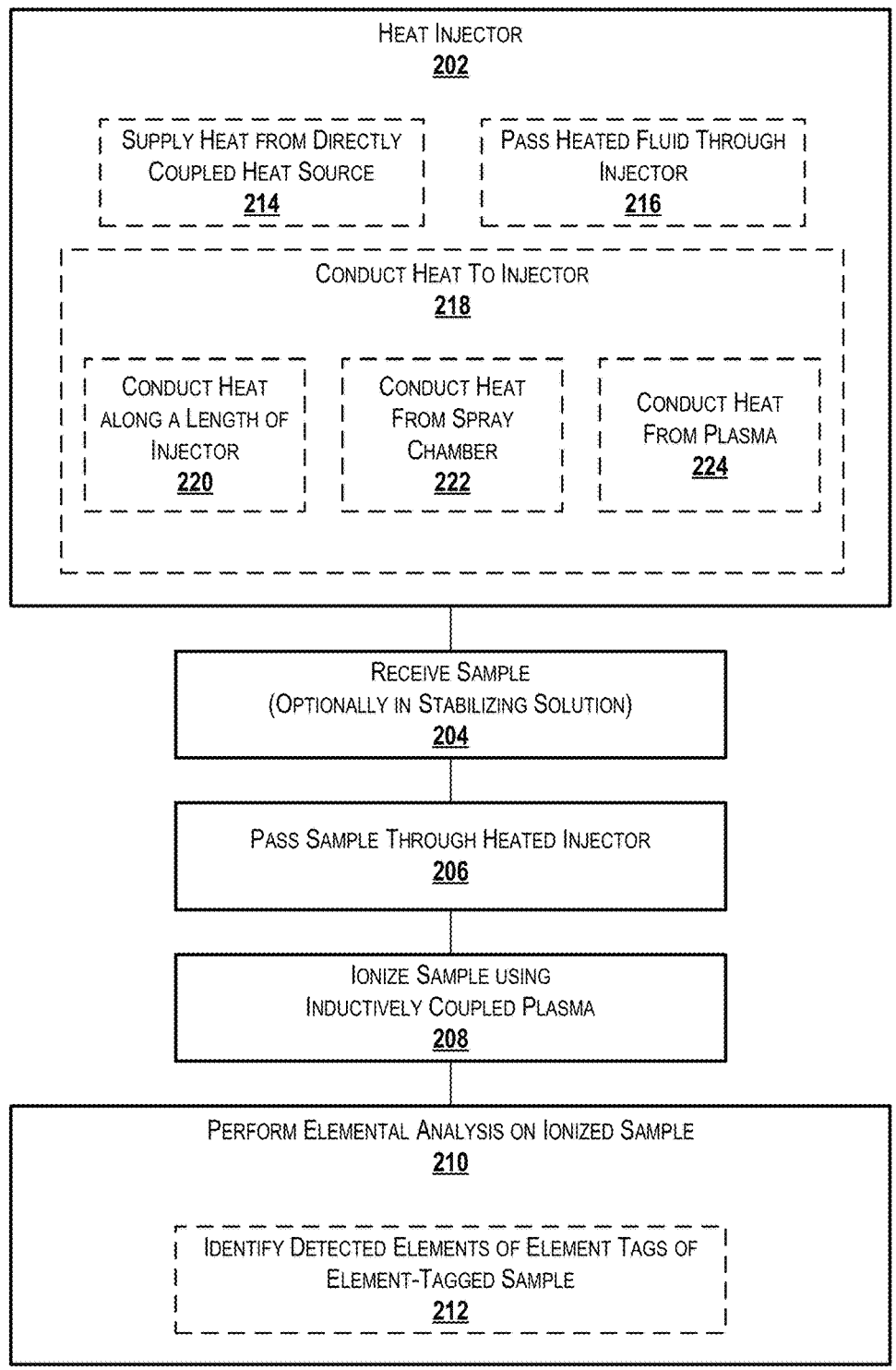
FIG. 2 is a flowchart depicting a process for ionizing a sample according to certain aspects of the present disclosure.

FIG. 2 is a flowchart depicting a process 200 for ionizing a sample according to certain aspects of the present disclosure. Process 200 can be carried out by any suitable ICP system as described herein, such as ICP system 100 of FIG. 1. At block 202, the injector can be heated. The injector can be heated according to any suitable technique, such as those described herein. In some cases, heating the injector at block 202 can include supplying heat to the injector from a directly coupled heat source at block 214 (e.g., supplying heat from a resistance heater wrapped around the injector). In some cases, heating the injector at block 202 can include passing heated fluid through the injector at block 216 (e.g., passing heated cell acquisition solution or another heated fluid through the injector).

In some cases, heating the injector at block 202 can include conducting heat to the injector at block 218. In some cases, conducting heat to the injector at block 218 can include conducting heat along a length of the injector at block 220. In some cases, conducting heat to the injector at block 218 can include conducting heat from a spray chamber of the ICP system at block 222. In some cases, conducting heat to the injector at block 218 can include conducting heat from plasma generated by the ICP system at block 224.

At block 204, the sample is received. The sample can optionally include the stabilizing solution. In some cases, receiving the sample at 204 can optionally include mixing the stabilizing solution with the sample. At block 206, the sample is passed through the heated injector. Passing the sample through the heated injector at block 206 can optionally include passing the sample through the heated injector as a part of a cell acquisition solution containing the sample and a stabilizing solution. Passing the sample through the heated injector at block 206 can include directing the sample to the plasma of the ICP system. In some cases, passing the sample through the heated injector at block 206 can include passing intact cells or whole cells through the injector. In some cases, intact cells or whole cells can be passed sequentially.

At block 208, the sample can be ionized using the inductively coupled plasma. Ionizing the sample at block 208 can result in the release of ions from the sample, such as a beam of ions. In some cases, ionizing the sample at block 208 can include ionizing intact cells or whole cells. In some cases, intact cells or whole cells can be ionized sequentially. At block 210, elemental analysis can be performed on the ionized sample. Performing elemental analysis at block 210 can include any suitable elemental analysis, such as measuring ions using a mass spectrometer (e.g., mass spectrometry) or detecting optical emissions during ionization of the sample (e.g., optical emission spectrometry). At optional block 212, detected elements can be identified based on the measurements of the elemental analysis. The detected elements can be tag atoms from element tags associated with the element-tagged sample (e.g., the sample labeled with element tags). In some cases, the detected elements identified at block 212 can be associated with an intact cell or whole cell. Identifying detected elements at block 212 for intact cells or whole cells can be repeated for multiple cells in a sample.

Figure 3:
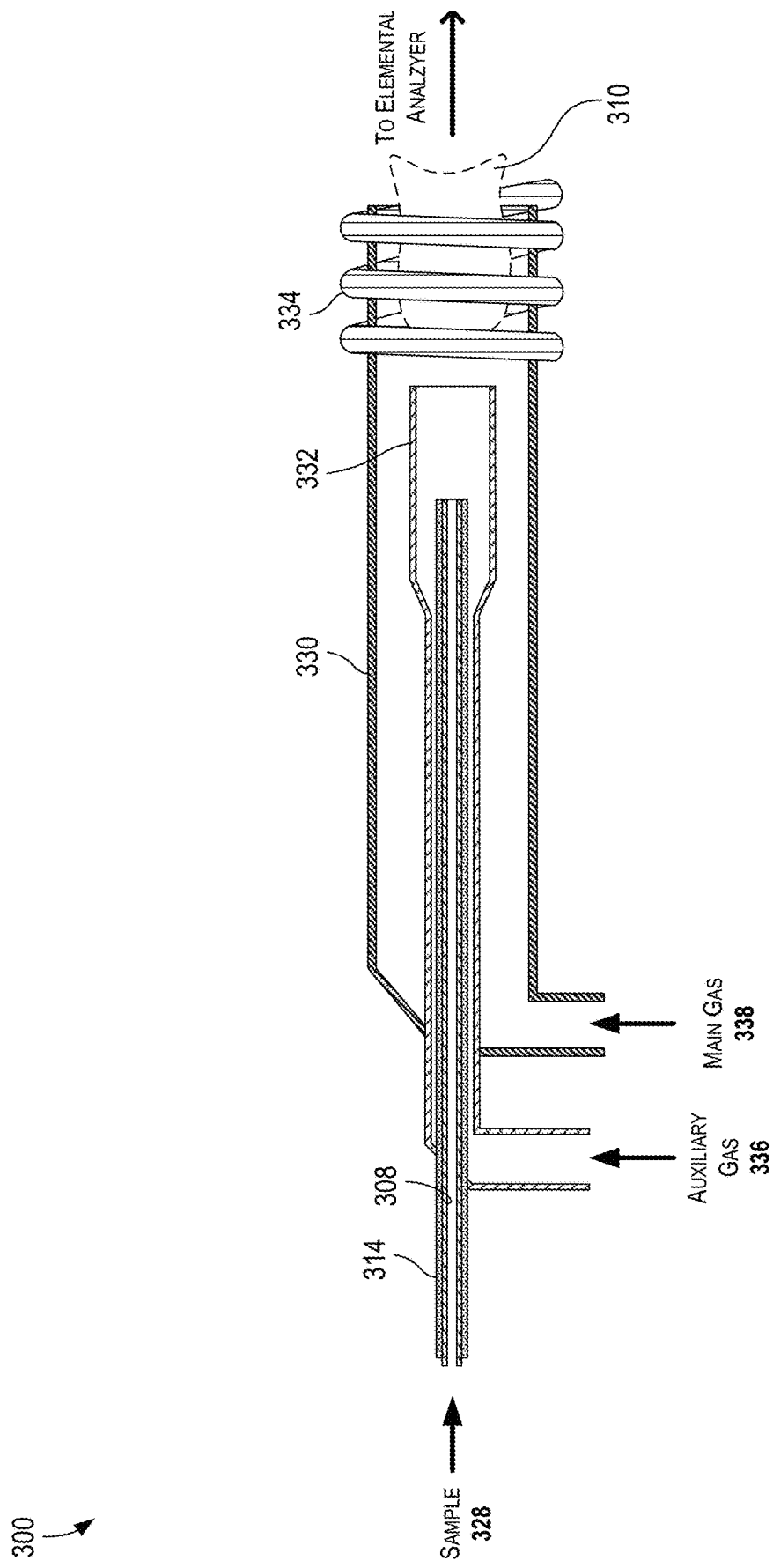
FIG. 3 is a schematic cross-sectional diagram depicting an ICP system with a heat transfer device thermally coupled to an injector according to certain aspects of the present disclosure.

FIG. 3 is a schematic cross-sectional diagram depicting an ICP system 300 with a heat transfer device 314 thermally coupled to an injector 308 according to certain aspects of the present disclosure. The ICP system 300 can include an outer tube 330 for conveying a main gas 338, such as argon. In some cases, a middle tube 332 can be used and can convey an auxiliary gas 336, such as argon. In some cases, the main gas 338 and the auxiliary gas 336 are the same, optionally with different flow rates. A coil 334 positioned towards the downstream end of the outer tube 330 can be energized with a high frequency current suitable to excite the gasses within the aperture of the coil 334 to create and/or maintain a plasma 310. A sample 328 (e.g., alone or part of a cell acquisition solution along with stabilizing solution) can enter the injector 308 and pass therethrough in a downstream direction (e.g., from left to right as depicted in FIG. 3). The sample 328 can be conveyed into the plasma 310. Resulting ions, light, or other detectable emissions or light absorption properties can be conveyed from the plasma 310 to an elemental analyzer. In some cases, the injector 308, outer tube 330, and optional middle tube 332 are concentric, although this need not always be the case.

As depicted in FIG. 3, the injector 308 can include a heat transfer device 314 coupled thereto both physically and thermally. The heat transfer device 314 is shown as extending to a downstream end of the injector 308, although this need not always be the case. The heat transfer device 314 can be used along with additional heat sources to heat the injector 308. In some cases, however, the heat transfer device 314 can simply convey heat throughout the injector 308.

In some cases, auxiliary gas 336 and/or main gas 338 can be pre-heated to convey heating to the injector 308.

Figure 4:
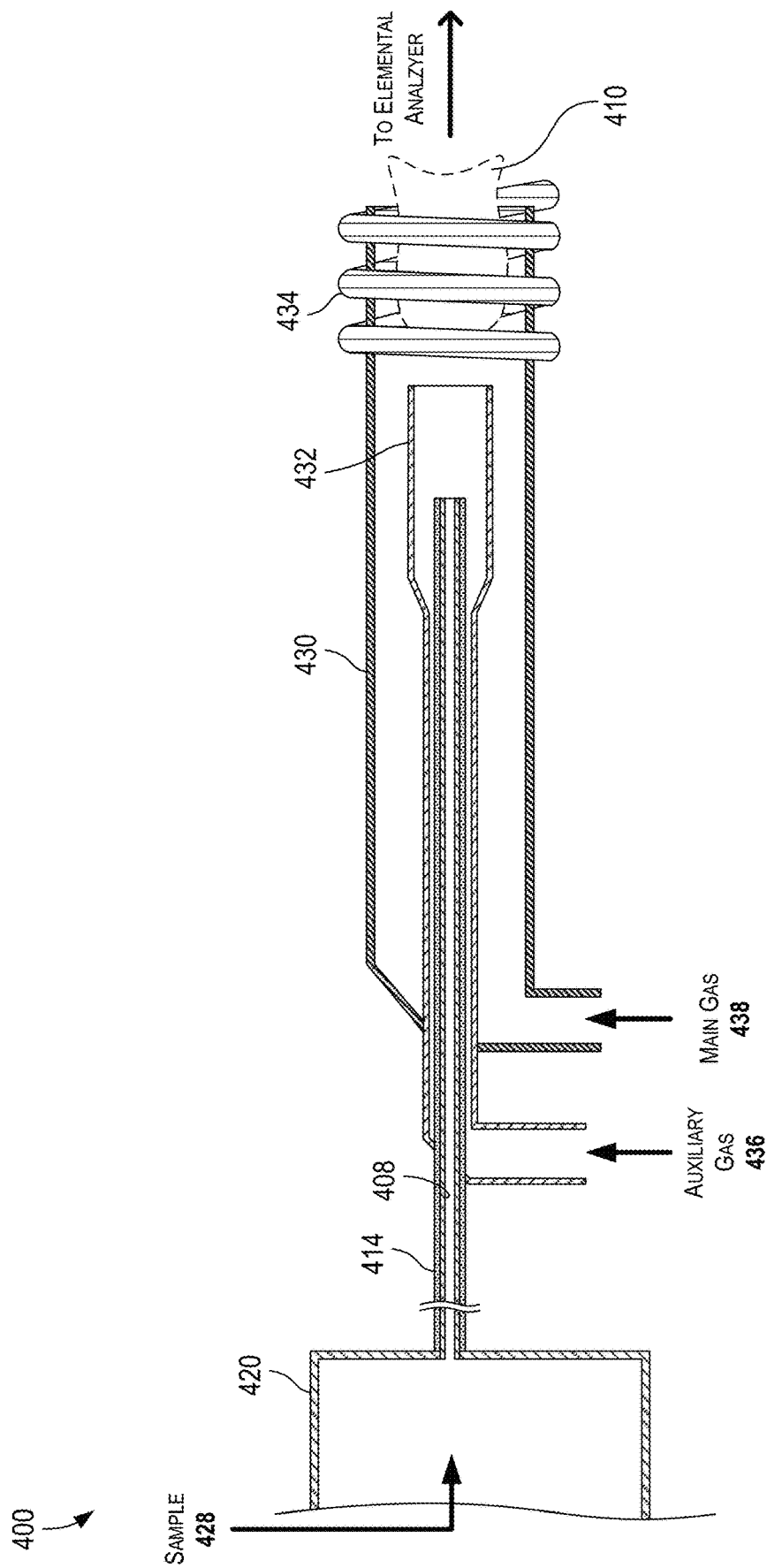
FIG. 4 is a schematic cross-sectional diagram depicting an ICP system with an injector thermally coupled to a spray chamber according to certain aspects of the present disclosure.

FIG. 4 is a schematic cross-sectional diagram depicting an ICP system 400 with an injector 408 thermally coupled to a spray chamber 420 according to certain aspects of the present disclosure. The ICP system 400 can include an outer tube 430 for conveying a main gas 438, such as argon. In some cases, a middle tube 432 can be used and can convey an auxiliary gas 436, such as argon. In some cases, the main gas 438 and the auxiliary gas 436 are the same, optionally with different flow rates. A coil 434 positioned towards the downstream end of the outer tube 430 can be energized with a high frequency current suitable to excite the gasses within the aperture of the coil 434 to create and/or maintain a plasma 410. A sample 428 (e.g., alone or part of a cell acquisition solution along with stabilizing solution) can enter the injector 408 and pass therethrough in a downstream direction (e.g., from left to right as depicted in FIG. 4). The sample 428 can be conveyed into the plasma 410. Resulting ions, light, or other detectable emissions or light absorption properties can be conveyed from the plasma 410 to an elemental analyzer. In some cases, the injector 408, outer tube 430, and optional middle tube 432 are concentric, although this need not always be the case.

As depicted in FIG. 4, the injector 408 can include a heat transfer device 414 coupled thereto both physically and thermally. The heat transfer device 414 is shown as extending from the spray chamber 420 to a downstream end of the injector 408, although in some cases the heat transfer device 414 may not extend this full length. The heat transfer device 414 can thermally couple the spray chamber 420 to the injector 408, conveying heat from the spray chamber 420 into the injector 408.

Figure 5:
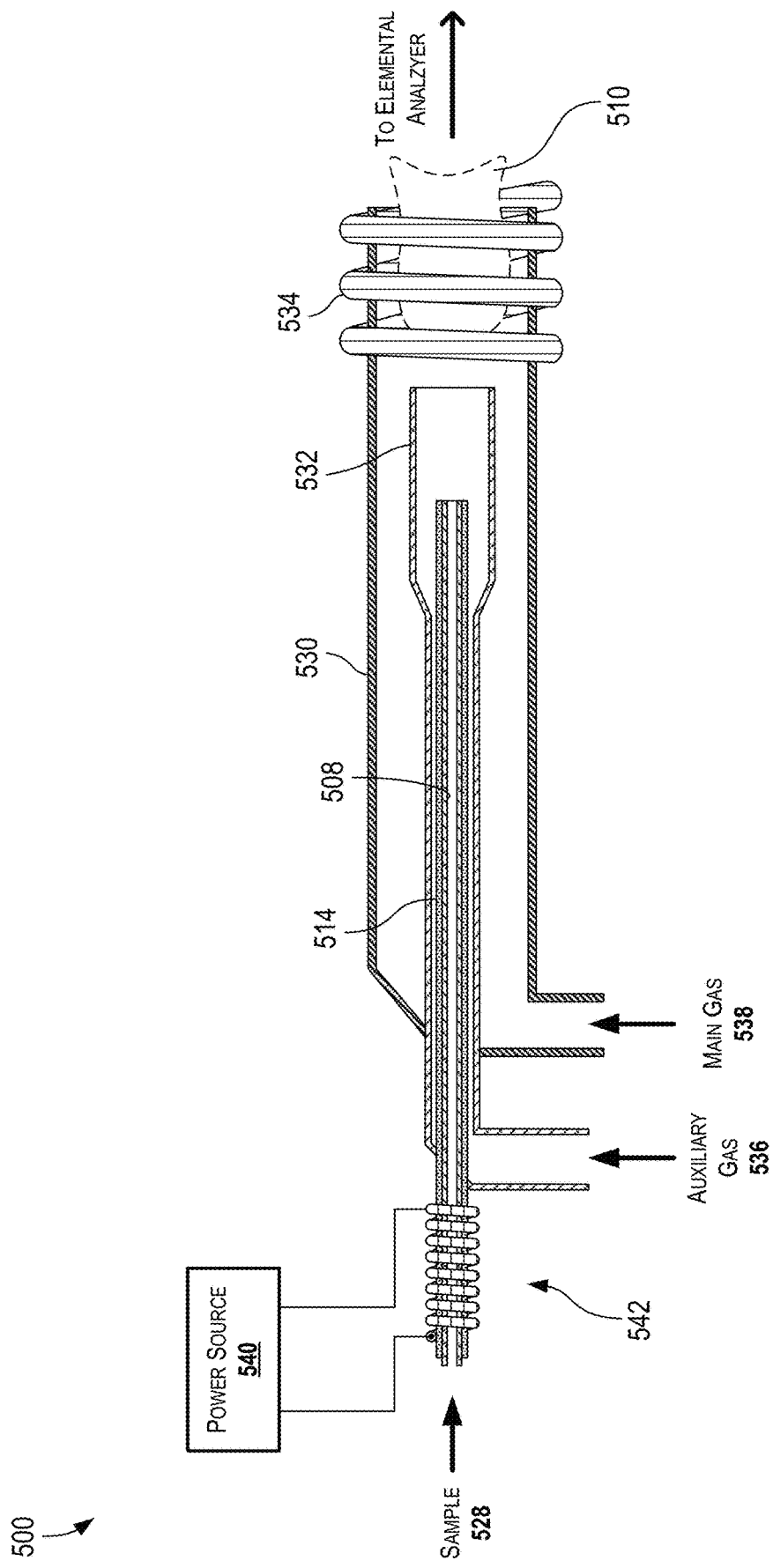
FIG. 5 is a schematic cross-sectional diagram depicting an ICP system with a heat source thermally coupled to an injector according to certain aspects of the present disclosure.

FIG. 5 is a schematic cross-sectional diagram depicting an ICP system 500 with a heat source 518 thermally coupled to an injector 508 according to certain aspects of the present disclosure. The ICP system 500 can include an outer tube 530 for conveying a main gas 538, such as argon. In some cases, a middle tube 532 can be used and can convey an auxiliary gas 536, such as argon. In some cases, the main gas 538 and the auxiliary gas 536 are the same, optionally with different flow rates. A coil 534 positioned towards the downstream end of the outer tube 530 can be energized with a high frequency current suitable to excite the gasses within the aperture of the coil 534 to create and/or maintain a plasma 510. A sample 528 (e.g., alone or part of a cell acquisition solution along with stabilizing solution) can enter the injector 508 and pass therethrough in a downstream direction (e.g., from left to right as depicted in FIG. 5). The sample 528 can be conveyed into the plasma 510. Resulting ions, light, or other detectable emissions or light absorption properties can be conveyed from the plasma 510 to an elemental analyzer. In some cases, the injector 508, outer tube 530, and optional middle tube 532 are concentric, although this need not always be the case.

As depicted in FIG. 5, the injector 508 can include a heat transfer device 514 coupled thereto both physically and thermally. The heat transfer device 514 is shown as extending along a length of the injector 508 up to a downstream end of the injector 508, although that need not always be the case. A resistive heater 542 is depicted around a portion of the injector 508, however in some cases, a resistive heater 542 can extend along the full length of the injector 508. The resistive heater 542 can be powered by a power source 540 to generate heat. The generated heat can be transferred to the injector 508 through the heat transfer device 514. The heat transfer device 514 can facilitate transmitting heat along the length of the injector 508, such as from the portion of the injector 508 around which the resistive heater 542 is positioned to the downstream end of the injector 508.

Figure 6:
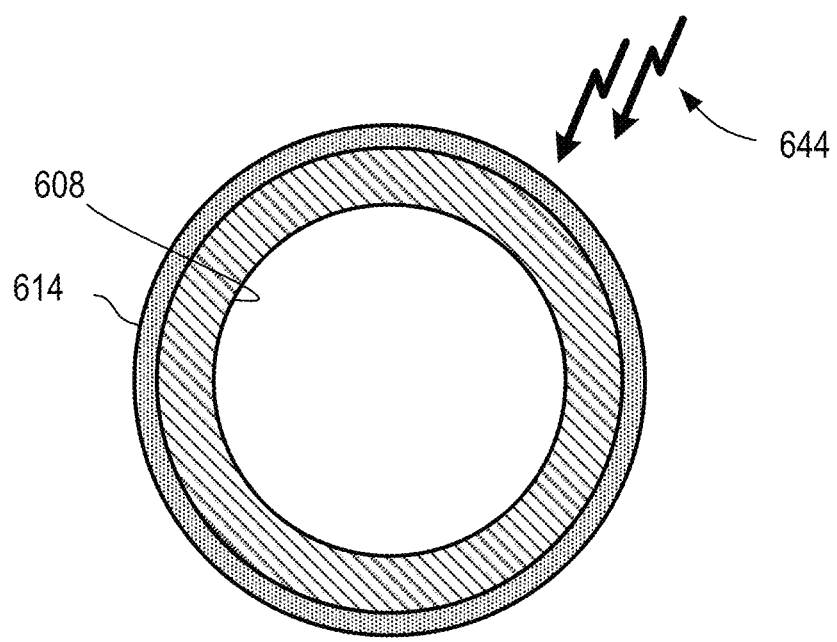
FIG. 6 is a schematic front cross-sectional diagram depicting an injector with a heat transfer device thermally coupled thereto according to certain aspects of the present disclosure.

FIG. 6 is a schematic front cross-sectional diagram depicting an injector 608 with a heat transfer device 614 thermally coupled thereto according to certain aspects of the present disclosure. Injector 608 can be similar to injector 308 of FIG. 3. The heat transfer device 614 can be physically coupled to the injector 608 or can be simply disposed around or adjacent the injector 608. The heat transfer device 614 can receive heat 644, such as from an external heat source, and transfer the heat 644 into the injector 608.

Figure 7:
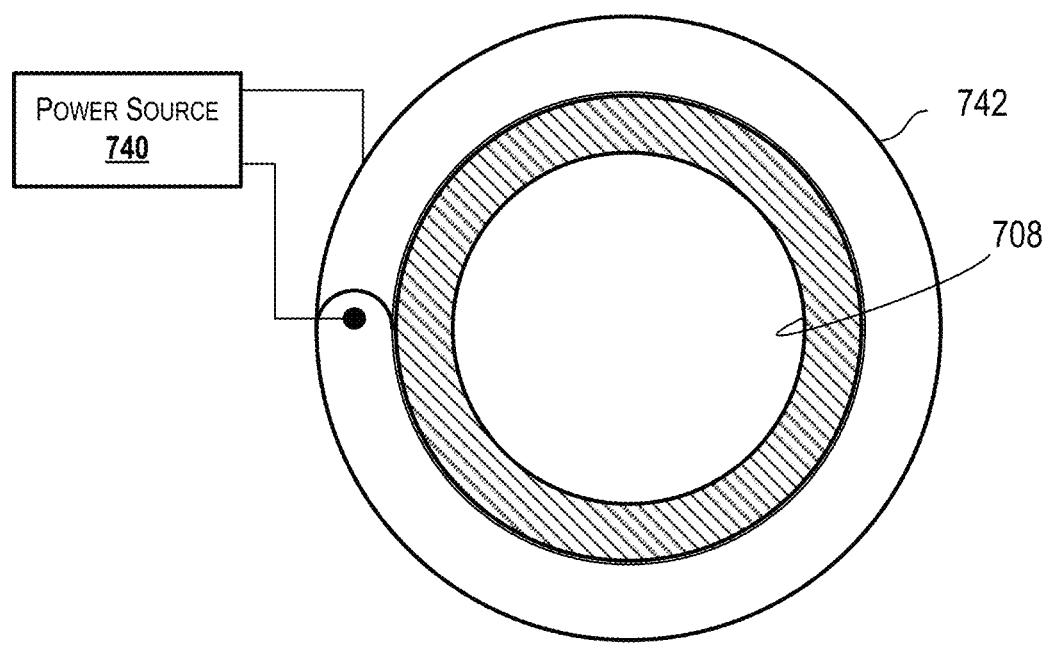
FIG. 7 is a schematic front cross-sectional diagram depicting an injector with a heat source thermally coupled thereto according to certain aspects of the present disclosure.

FIG. 7 is a schematic front cross-sectional diagram depicting an injector 708 with a heat source 718 thermally coupled thereto according to certain aspects of the present disclosure. Injector 708 can be similar to injector 508 of FIG. 5, however without the heat transfer device 514. A resistive heater 742 in the form of a coil can be disposed around, and optionally physically coupled to, the injector 708. Upon application of power from power source 740 to the resistive heater 742, the resistive heater 742 can generate heat to heat the injector 708.

Figure 8:
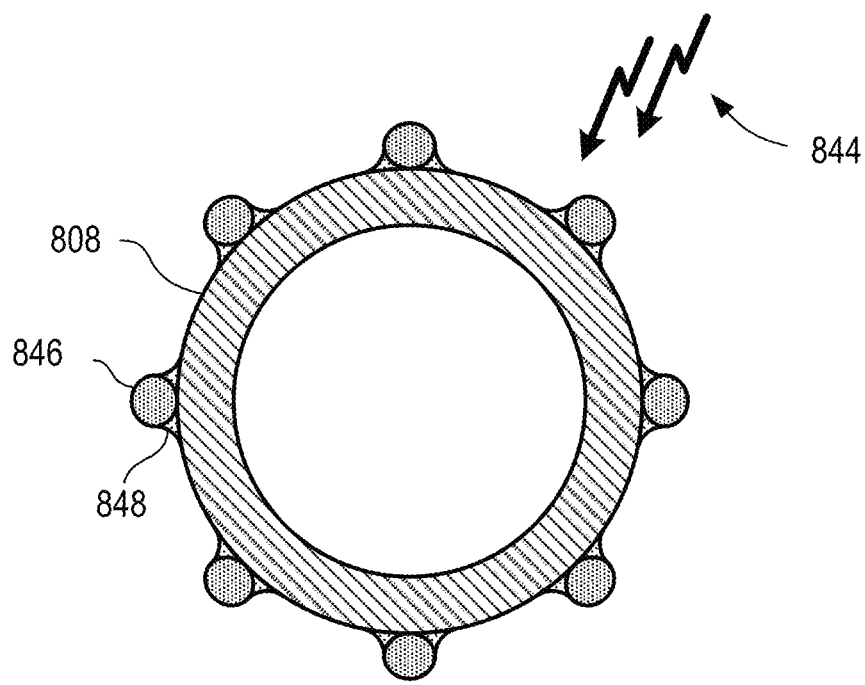
FIG. 8 is a schematic front cross-sectional diagram depicting an injector with external heat pipes thermally coupled thereto according to certain aspects of the present disclosure.

FIG. 8 is a schematic front cross-sectional diagram depicting an injector 808 with external heat pipes 846 thermally coupled thereto according to certain aspects of the present disclosure. The heat pipes 846 can be types of thermal transfer devices, capable of conveying heat 844 into the injector 808. In some cases, the heat pipes 846 can be thermally coupled to the injector 808 using thermal paste 848. In some cases, heat pipes 846 can be located on internal surfaces of the injector 808. Heat pipes 846 can extend along part of or all of the length of the injector 808.

Figure 9:
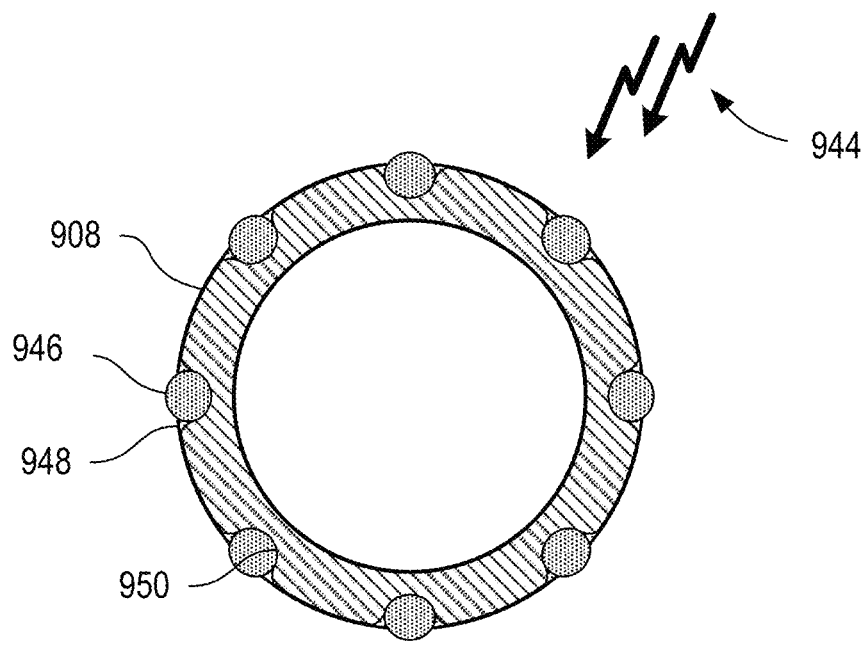
FIG. 9 is a schematic front cross-sectional diagram depicting an injector with internal heat pipes thermally coupled thereto according to certain aspects of the present disclosure.

FIG. 9 is a schematic front cross-sectional diagram depicting an injector 908 with internal heat pipes 946 thermally coupled thereto according to certain aspects of the present disclosure. The heat pipes 946 can be types of thermal transfer devices, capable of conveying heat 944 into the injector 908. In some cases, the heat pipes 946 can be thermally coupled to the injector 908 using thermal paste 948. Heat pipes 946 can be located within channels 950 of the injector 908. In some cases, heat pipes 946 can be fully enclosed by the injector 908, including cross-sectionally enclosed and/or longitudinally enclosed. In some cases, heat pipes 946 can be located in channels 950 located on internal surfaces of the injector 908. Heat pipes 946 can extend along part of or all of the length of the injector 908.

Figure 10:
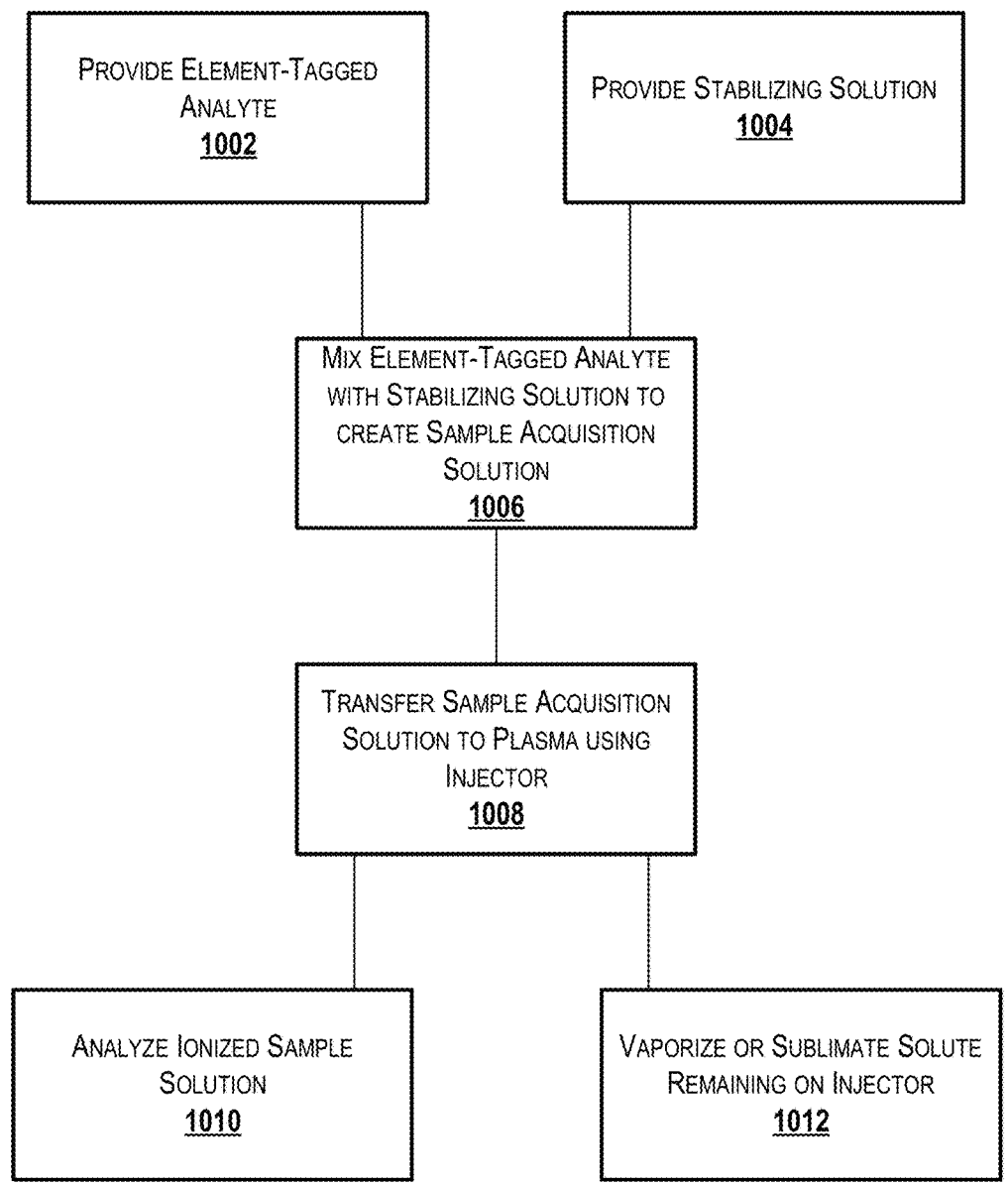
FIG. 10 is a flowchart depicting a process for preparing and ionizing a sample according to certain aspects of the present disclosure.

FIG. 10 is a flowchart depicting a process 1000 for preparing and ionizing a sample according to certain aspects of the present disclosure. Process 100 can utilize any suitable ICP system, such as ICP system 100 of FIG. 1. At block 1002, an element-tagged analyte is provided. An element-tagged analyte can include analytes on or within whole cells or intact cells that have been tagged or labeled with an element tag. At block 1004, a stabilizing solution can be provided. The stabilizing solution can be any suitable stabilizing solution as described herein, such as a solution containing 15 mM of ammonium nitrate. At block 1006, the element-tagged analyte can be mixed with the stabilizing solution to create a sample acquisition solution (e.g., cell acquisition solution).

The sample acquisition solution can include intact cells or whole cells in suspension with a stabilizing solution containing salt, such as ammonium nitrate, as described herein. The intact cells or whole cells of the sample acquisition solution can be labeled with element tags, such as by containing element-tagged analytes.

At block 1008, the sample acquisition solution is transferred to a plasma of an ICP system using an injector at block 1008. The sample acquisition solution can be pressurized through the injector using a fluid, such as the sample acquisition solution and/or a carrier gas. In some cases, transferring the sample acquisition solution to the plasma using the injector can include passing the sample acquisition solution through a heated injector and/or heating the injector.

At block 1010, the ionized sample solution can be analyzed, such as through elemental analysis (e.g., mass spectrometry or optical emission spectrometry). In some cases, at optional block 1012, solute remaining on the injector, such as from the stabilizing solution, can be vaporized or sublimated. Vaporization or sublimation of the solute can be achieved through heating of the injector. In some cases, vaporization or sublimation of the solute at block 1012 can occur subsequent to or simultaneous with transferring the sample acquisition solution to the plasma using the injector at block 1008.

Figure 11:
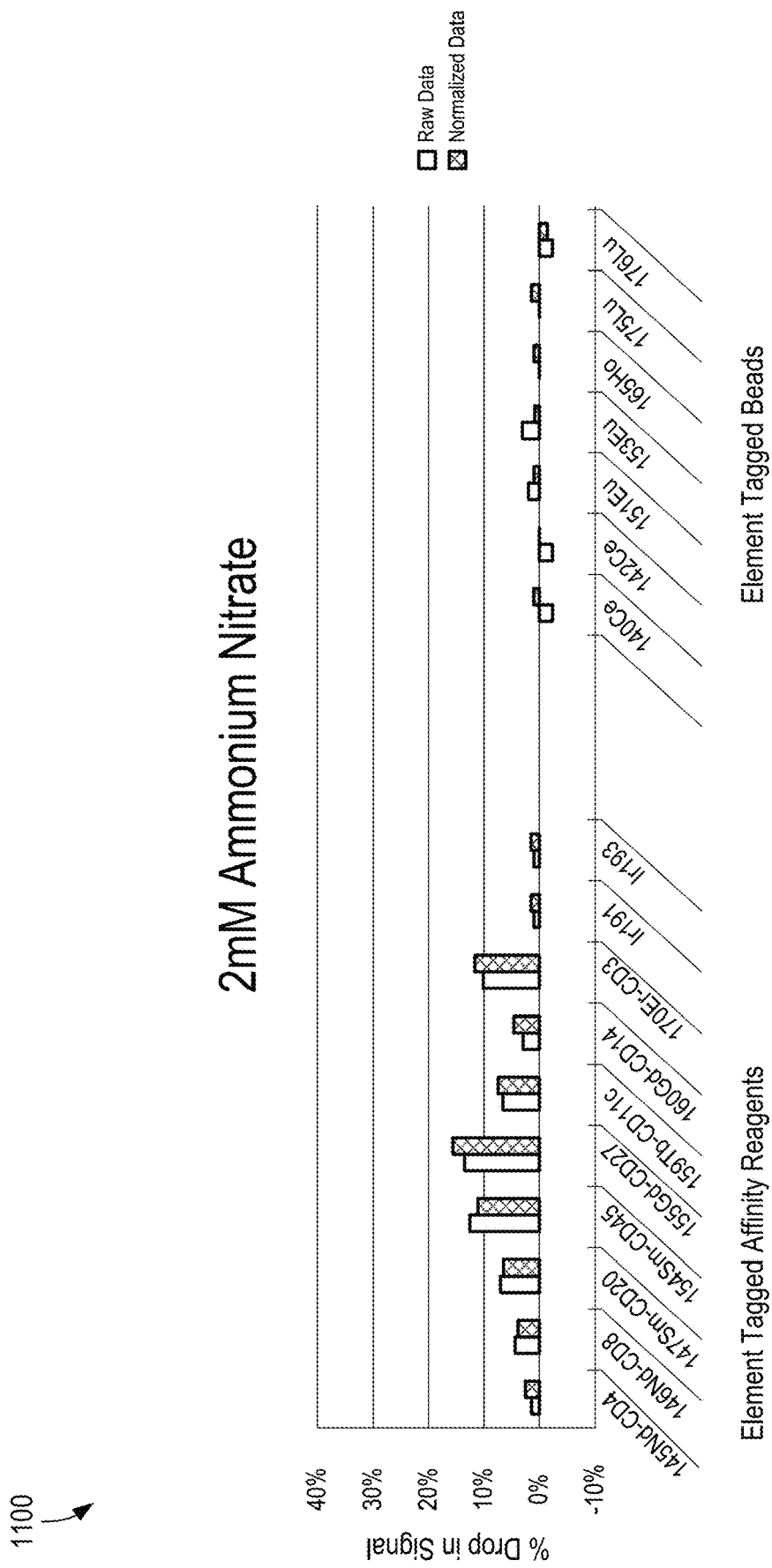
FIG. 11 is a chart depicting the percentage drop in signal for a set of samples prepared with a 2 mM ammonium nitrate stabilizing solution according to certain aspects of the present disclosure.
Figure 12:
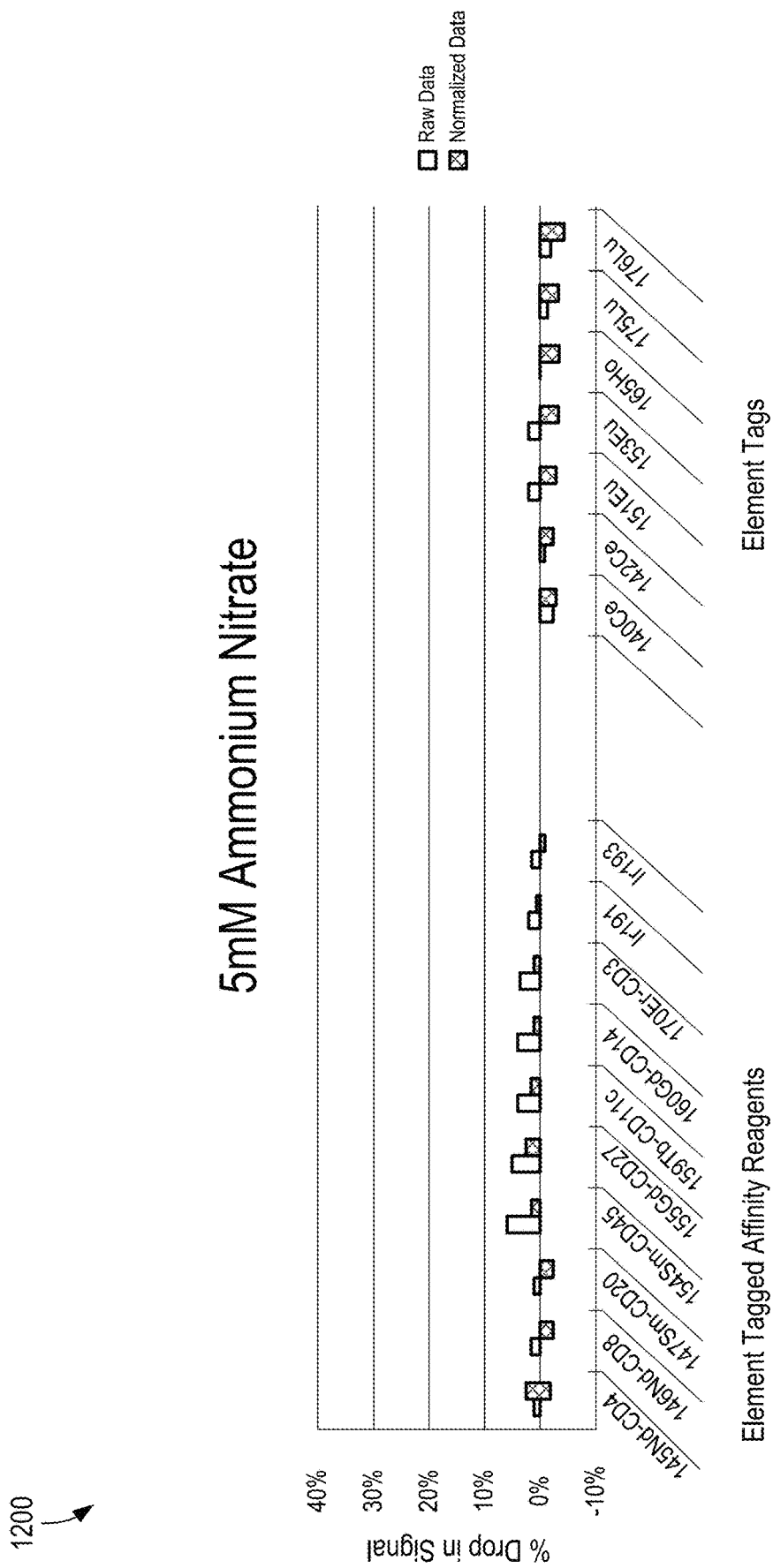
FIG. 12 is a chart depicting the percentage drop in signal for a set of samples prepared with a 5 mM ammonium nitrate stabilizing solution according to certain aspects of the present disclosure.
Figure 13:
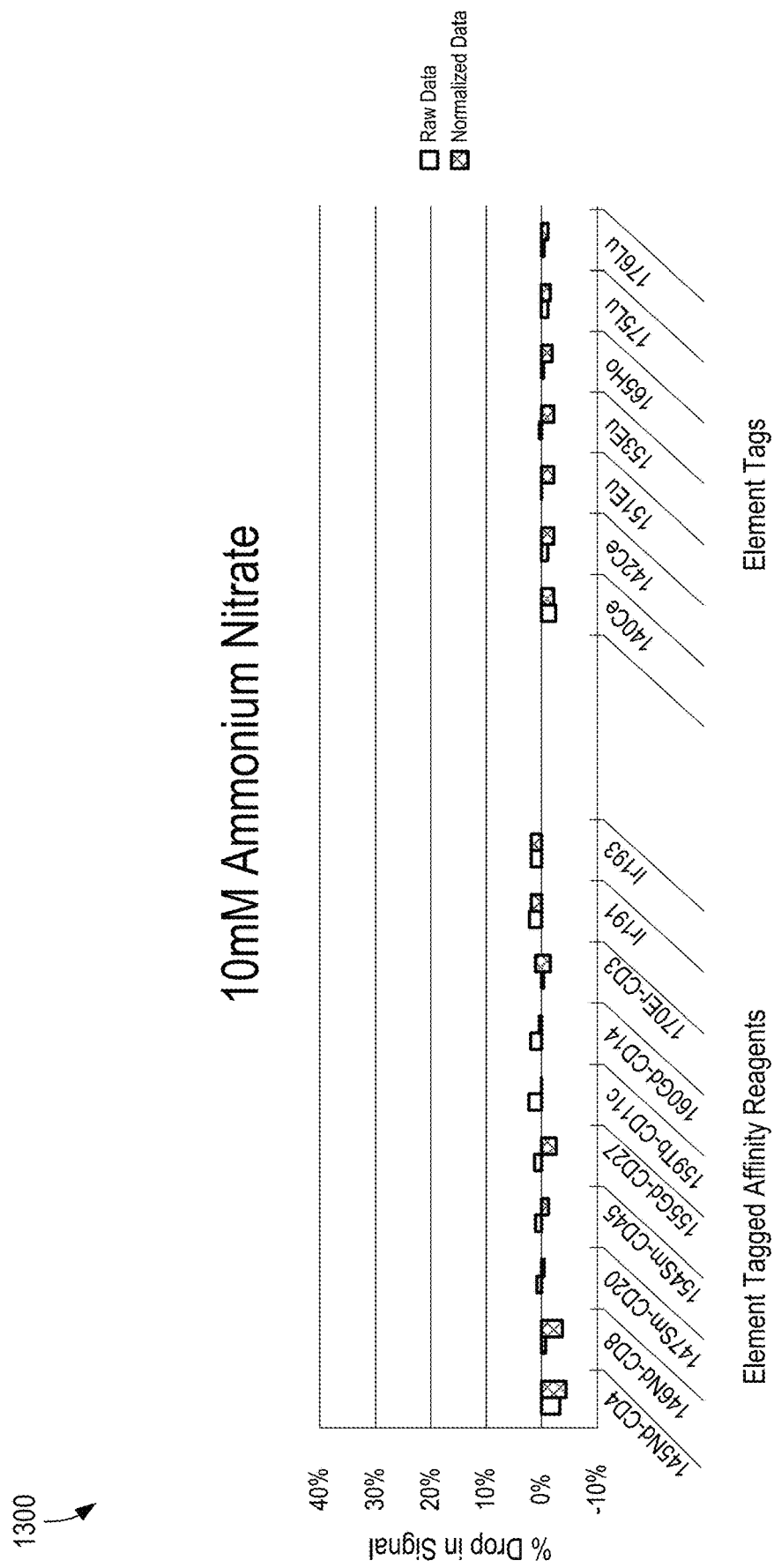
FIG. 13 is a chart depicting the percentage drop in signal for a set of samples prepared with a 10 mM ammonium nitrate stabilizing solution according to certain aspects of the present disclosure.

FIGS. 11-13 depict charts 1100, 1200, 1300 that illustrate percent drop in signal for a particular sample when prepared with ammonium nitrate stabilizing solutions of various molarities. The sample contains various element-tagged affinity reagents and element-tagged beads. The element-tagged affinity reagents in this sample include 145Nd-CD4 (an affinity reagent specific to the CD4 antigen and containing the element tag $^{145}$Nd), 145Nd-CD4 (an affinity reagent specific to the CD4 antigen and containing the element tag $^{145}$Nd), 146Nd-CD8 (an affinity reagent specific to the CD8 antigen and containing the element tag $^{148}$Nd), 147Sm-CD20 (an affinity reagent specific to the CD20 antigen and containing the element tag $^{147}$Sm), 154Sm-CD45 (an affinity reagent specific to the CD45 antigen and containing the element tag $^{154}$Sm), 155Gd-CD27 (an affinity reagent specific to the CD27 antigen and containing the element tag $^{155}$Gd), 159Tb-CD11c (an affinity reagent specific to the CD11c antigen and containing the element tag $^{159}$Tb), 160Gd-CD14 (an affinity reagent specific to the CD14 antigen and containing the element tag $^{160}$Gd), 170Er-CD3 (an affinity reagent specific to the CD3 antigen and containing the element tag $^{170}$Er), Ir191 (an affinity reagent specific to a first identifiable DNA strain and containing the element tag $^{191}$Ir), and IR193 (an affinity reagent specific to a second identifiable DNA strain and containing the element tag $^{193}$Ir). The element-tagged beads in this sample include beads containing known quantities of $^{140}$Ce, $^{142}$Ce $^{151}$Eu, $^{153}$Eu, $^{165}$Ho, $^{175}$Lu, $^{176}$Lu. Each of the aforementioned elements or isotopes can be measured by an elemental analyzer. In some cases, each of the aforementioned elements or isotopes can be measured using distinct channels of the elemental analyzer that are specific to only that element or isotope.

In each of charts 1100, 1200, and 1300, the percent signal drop in the raw data measurements over the course of the sample run (e.g., a 30 minute sample run) are shown along with the percent signal drop after the data has been normalized. Data normalization can include adjusting measured signal intensity for various channels of the elemental analyzer based on a detected signal drift in a known standard. In some cases, one or more element-tagged beads, such as those identified above, can be used as known standards. For example, if the element-tagged beads containing $^{165}$Ho were used as a known standard, the element-tagged beads may contain a known quantity of $^{165}$Ho and may be present in a known concentration, which should result in a constant signal intensity across the sample run. To the extent any drift from the expected signal intensity is detected, corrections can be applied to bring the $^{165}$Ho signal back to the expected signal intensity and similar corrections can be made to the other channels of the elemental analyzer. In some cases, element-tagged beads can be normalized to other element-tagged beads, even in a common time interval, such as to account for moment-to-moment drift in the detector of the elemental analyzer in that time interval.

FIG. 11 is a chart 1100 depicting the percentage drop in signal for a set of samples prepared with a 2 mM ammonium nitrate stabilizing solution according to certain aspects of the present disclosure. The chart 1100 shows the percentage drop in signal across numerous element-tagged affinity reagents when the sample is prepared with a 2 mM ammonium nitrate stabilizing solution. As depicted in chart 1100, the percent drop in signal remains below approximately 15% for nearly all channels and below approximately 10% or 5% for many channels.

FIG. 12 is a chart 1200 depicting the percentage drop in signal for a set of samples prepared with a 5 mM ammonium nitrate stabilizing solution according to certain aspects of the present disclosure. The chart 1200 shows the percentage drop in signal across numerous element-tagged affinity reagents when the sample is prepared with a 5 mM ammonium nitrate stabilizing solution. When compared with chart 1100 for the 2 mM ammonium nitrate stabilizing solution, it is apparent that the increase to a 5 mM ammonium nitrate stabilizing solution results in reduced signal drift. As depicted in chart 1200, the percent drop in signal remains below approximately 6% for all channels and below approximately 2% or 3% for most channels.

FIG. 13 is a chart 1300 depicting the percentage drop in signal for a set of samples prepared with a 10 mM ammonium nitrate stabilizing solution according to certain aspects of the present disclosure. The chart 1300 shows the percentage drop in signal across numerous element-tagged affinity reagents when the sample is prepared with a 10 mM ammonium nitrate stabilizing solution. When compared with chart 1200 for the 5 mM ammonium nitrate stabilizing solution, it is apparent that the increase to a 10 mM ammonium nitrate stabilizing solution does not impact stability to a large degree. As depicted in chart 1300, the percent drop in signal remains below approximately 4% or 5% for all channels and below approximately 1% or 2% for most channels.

Figure 15:
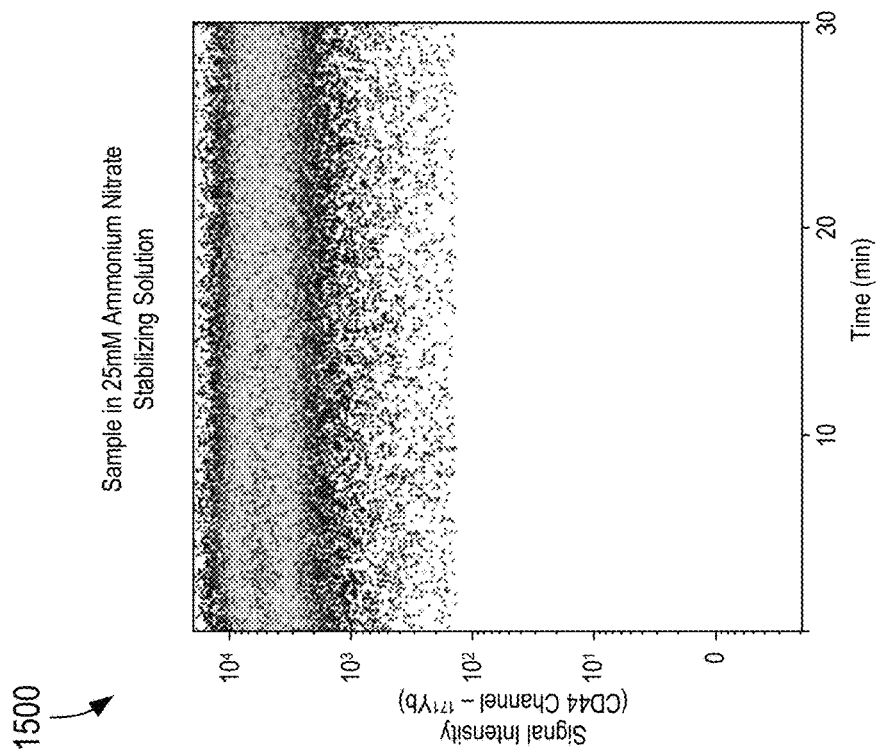
FIG. 15 is a chart depicting the signal of a CD44 channel for the sample of FIG. 14 having been suspended in 25 mM ammonium nitrate stabilizing solution and injected to a plasma source according to certain aspects of the present disclosure.
Figure 14:
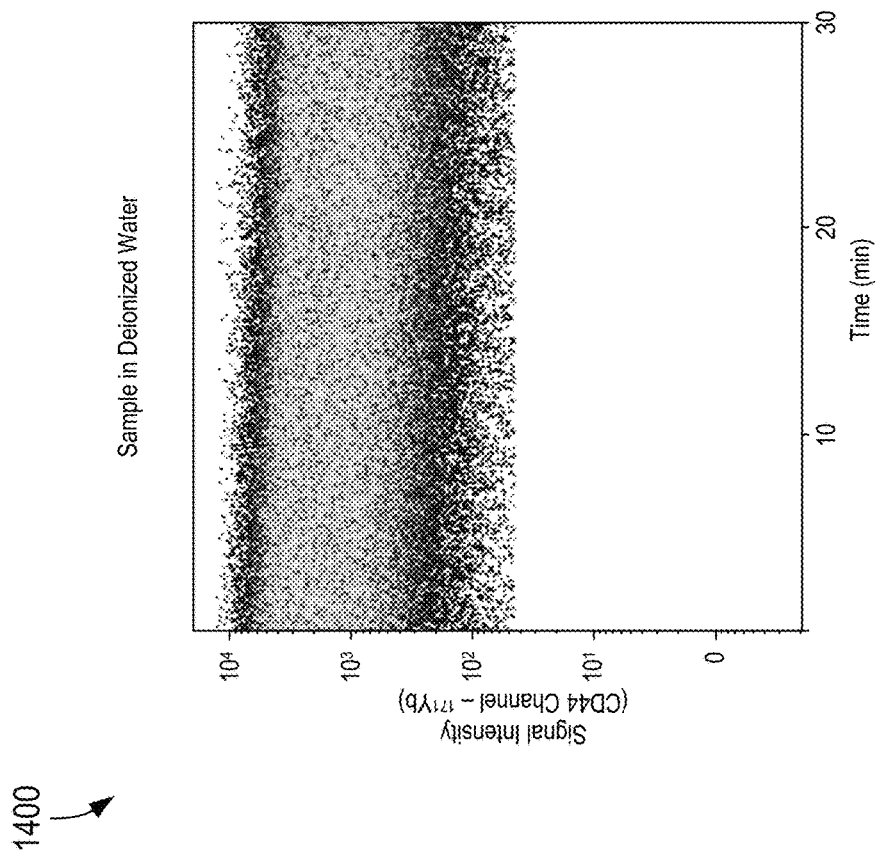
FIG. 14 is a chart depicting the signal of a CD44 channel for a sample having been suspended in deionized water and injected to a plasma source.

FIGS. 14 and 15 depict charts 1400, 1500 that show signal intensities within particular channels of elemental analyzers over the course of 30-minute sample runs. The particular channels are used in this case to identify CD44 antigens. The element-tagged affinity reagent specific for CD44 was tagged with $^{171}$Yb. The sample used during the 30 minute sample runs with respect to FIGS. 14 and 15 contained cells labeled with this element-tagged affinity reagent due to its specificity for CD44. The CD44 channels of the elemental analyzer are responsive to ions having atomic masses at or approximately the same as $^{171}$Yb, or at or approximately 171 amu. For each of charts 1400 and 1500, the x-axis represents time over the course of the elemental analysis and the y-axis represents intensity of expression (e.g., number of tag atoms detected) for the selected CD44 channel for detected events (each event is represented by a dot on the plot). These particular channels, antigens, and/or elements are selected to provide an example, however any other suitable channels, antigens, and/or elements can be used.

FIG. 14 is a chart 1400 depicting the signal of the CD44 channel for the sample having been suspended in deionized water and injected to a plasma source. The lighter region in the upper-middle of the band of measurements represents the population of the most frequent cell events. A relatively wide variation and a downward trend in y axis are evident in chart 1400, indicating some degree of cell instability during storage and/or injection. The downward trend can also be indicative of buildup occurring within the injector tube, which can negatively affect signal intensity over time. Further, if damage occurred to cells in this non-stabilized sample during storage and/or injection, element-tagged affinity reagents may have separated from the remainder of the cell to which they were attached, which may have created undesirable fluctuations in signal intensities as tag atoms that were expected to have fallen on the detector in close temporal proximity with other tag atoms for that particular cell may have instead ended up falling on the detector earlier or later. Therefore, a portion of that signal was not counted in the responses of individual events. As a result, the measurements depicted in chart 1400 can occupy a relatively wide band across the y-axis.

FIG. 15 is a chart 1500 depicting the signal of the CD44 channel for the sample having been suspended in 25 mM ammonium nitrate stabilizing solution and injected to a plasma source according to certain aspects of the present disclosure. The lighter region in the upper-middle of the band of measurements represents the population of the most frequent cell events. The effect of the stabilizing solution is evident in the substantially different clustering of the measured signal intensities in charts 1400 (e.g., without stabilizing solution) and 1500 (e.g., with stabilizing solution). The band of measured signals depicted in chart 1500 is much narrower than that of chart 1400, indicating a substantial increase in stability, which can be indicative of fewer or no cells being damaged during storage and/or injection. The band in chart 1500 provides a denser packing of measurements and a more clear and resolved average. Further, the band in chart 1500 shows a relatively constant, horizontal trend, as opposed to the downward trend of the band in chart 1400.

Figure 17:
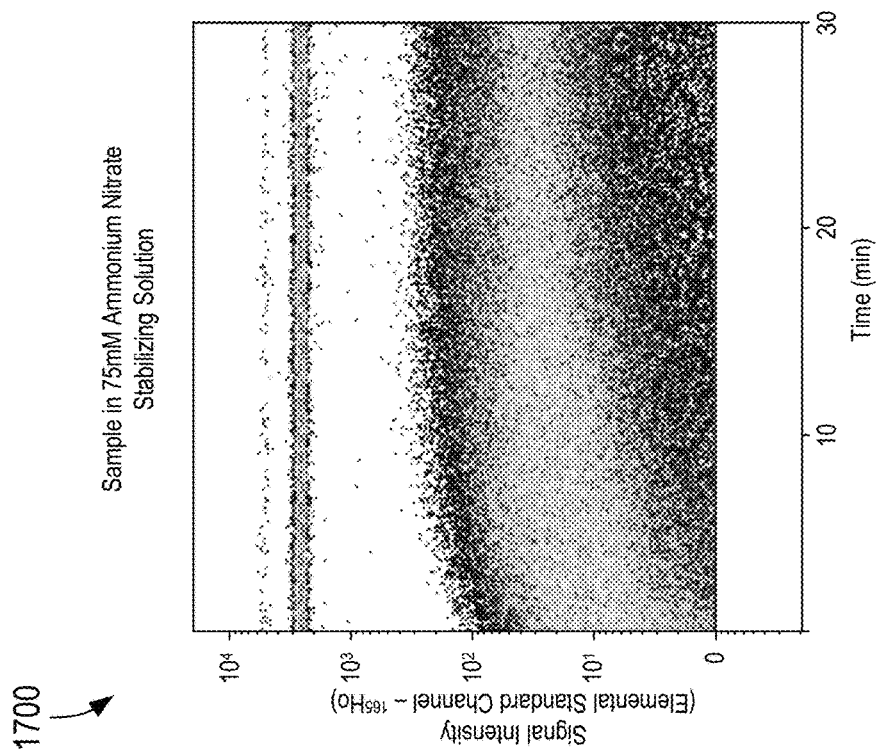
FIG. 17 is a chart depicting the signal of a $^{165}$Ho channel for the sample of FIG. 16 having been suspended in 75 mM ammonium nitrate stabilizing solution and injected to a plasma source according to certain aspects of the present disclosure.
Figure 16:
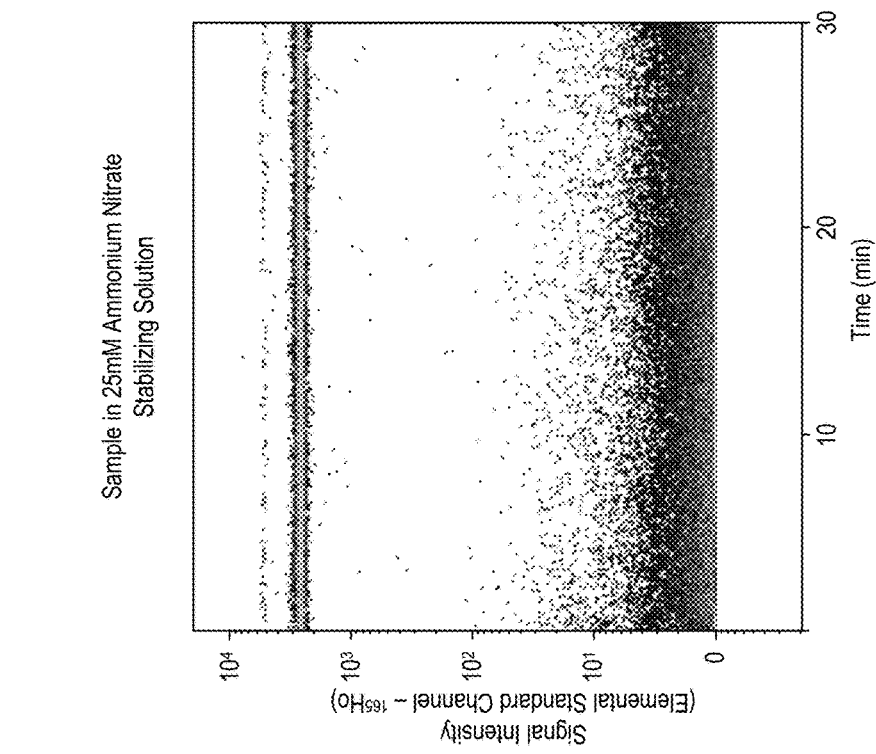
FIG. 16 is a chart depicting the signal of a $^{165}$Ho channel for a sample having been suspended in a 25 mM ammonium nitrate stabilizing solution and injected to a plasma source according to certain aspects of the present disclosure.

FIGS. 16 and 17 depict charts 1600, 1700 that show signal intensities within particular channels of elemental analyzers over the course of 30 minute sample runs. The particular channels are used in this case to identify elemental standards in the form of element-tagged beads. The element-tagged beads used with charts 1600 and 1700 are $^{165}$Ho. The channels used to obtain signal intensities depicted in charts 1600 and 1700 are responsive to ions having atomic masses at or approximately the same as $^{165}$Ho, or at or approximately 165 amu. The sample used during the 30 minute sample runs with respect to FIGS. 16 and 17 contained cells being sampled and the element-tagged beads. The $^{165}$Ho element-tagged bead was selected as an elemental standard since no $^{165}$Ho was present in the cells or in any element-tagged affinity reagents used along with the cells. For each of charts 1600 and 1700, the x-axis represents time over the course of the elemental analysis and the y-axis represents intensity of expression (e.g., number of tag atoms detected) for the selected $^{165}$Ho channels. These particular channels and/or elements are selected to provide an example, however any other suitable channels and/or elements can be used. In some cases, element-tagged beads selected to be elemental standards, which can contain any suitable element or isotope, such as $^{165}$Ho as described above, can be used to normalize signal intensity in the detector of the analyzer. An element-tagged bead containing a known quantity of an element or isotope can be expected to present a known quantity of tag atoms to the detector over a period of time, and thus any drift in signal intensity due to the natural drift in the detector can be identified if the signal for the element-tagged bead drops below the expected signal intensity, and thus the identified drift can be used to correct or normalize the signal intensities in other channels.

FIG. 16 is a chart 1600 depicting the signal of the $^{165}$Ho channel for the sample having been suspended in a 25 mM ammonium nitrate stabilizing solution and injected to a plasma source according to certain aspects of the present disclosure. The dense collection of measurements forming a thin band near the top of the chart 1600 is representative of those events correlated with the element-tagged beads and the large band of measurements near the bottom of the chart 1600 is representative of background noise from cell events in the 25 mM ammonium nitrate stabilizing solution. Since there is no source of $^{165}$Ho in the cells of the sample, the only source of measurements in the selected channel should be the element-tagged beads. Thus, as expected, the background noise in chart 1600 is relatively minimal and shows no regions of high intensity other than at the expected intensity for the element-tagged beads and at 0 (e.g., the expected intensity for the atoms of the cells in the sample). At 25 mM ammonium nitrate, the background signal does not overwhelm the signal of interest and the signal of interest is clearly distinguishable.

FIG. 17 is a chart 1700 depicting the signal of the $^{165}$Ho channel for the sample having been suspended in 75 mM ammonium nitrate stabilizing solution and injected to a plasma source according to certain aspects of the present disclosure. The thin band near the top of the chart 1700 is representative of those measurements correlated with the element-tagged beads and the large band of measurements near the bottom of the chart 1700 is representative of background noise in the 75 mM ammonium nitrate stabilizing solution. At 75 mM ammonium nitrate, the background signal is starting to overwhelm the signal of interest, and may begin to interfere with the ability to clearly distinguish the signal of interest. Specifically, the population of readings that are expected to be at or around an intensity of 0 are instead showing intensities above 0, suggestive that the detector is detecting $^{165}$Ho from a source other than the element-tagged beads. Since no $^{165}$Ho exists in the cells or stabilizing solution, it is apparent that the background signal is interfering with detection in the elemental analyzer.

When compared with chart 1600, chart 1700 shows that as higher concentrations of ammonium nitrate (or other salts) are used, it can begin to cause undesirable background interference. Therefore, it can be desirable to provide a stabilizing solution sufficiently high to improve cell stability, but sufficiently low to avoid overwhelming background interference.

Figure 18:
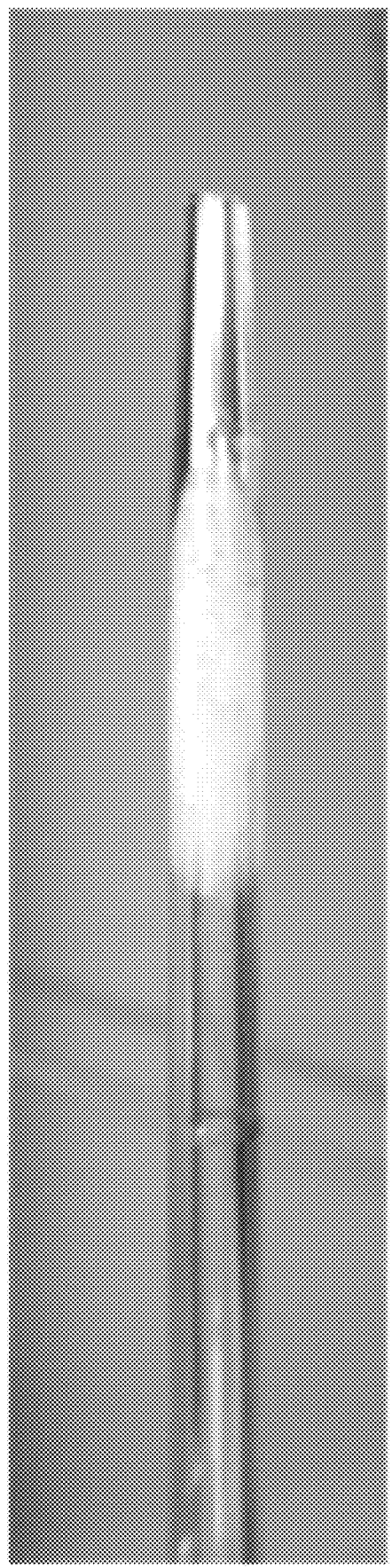
FIG. 18 is an image of buildup on an injector when used without sufficient heating of certain aspects of the present disclosure.

FIG. 18 is an image of an injector 1800 depicting substantial buildup due to use without sufficient heating of certain aspects of the present disclosure. The injector 1800 has not been heated or has been heated insufficiently and thus residue has built up within the injector. The residue may be a result of the salt of a stabilizing solution. It can be desirable to heat an injector when a stabilizing solution is used so as to avoid the buildup of residue as depicted in FIG. 18.

Figure 19:
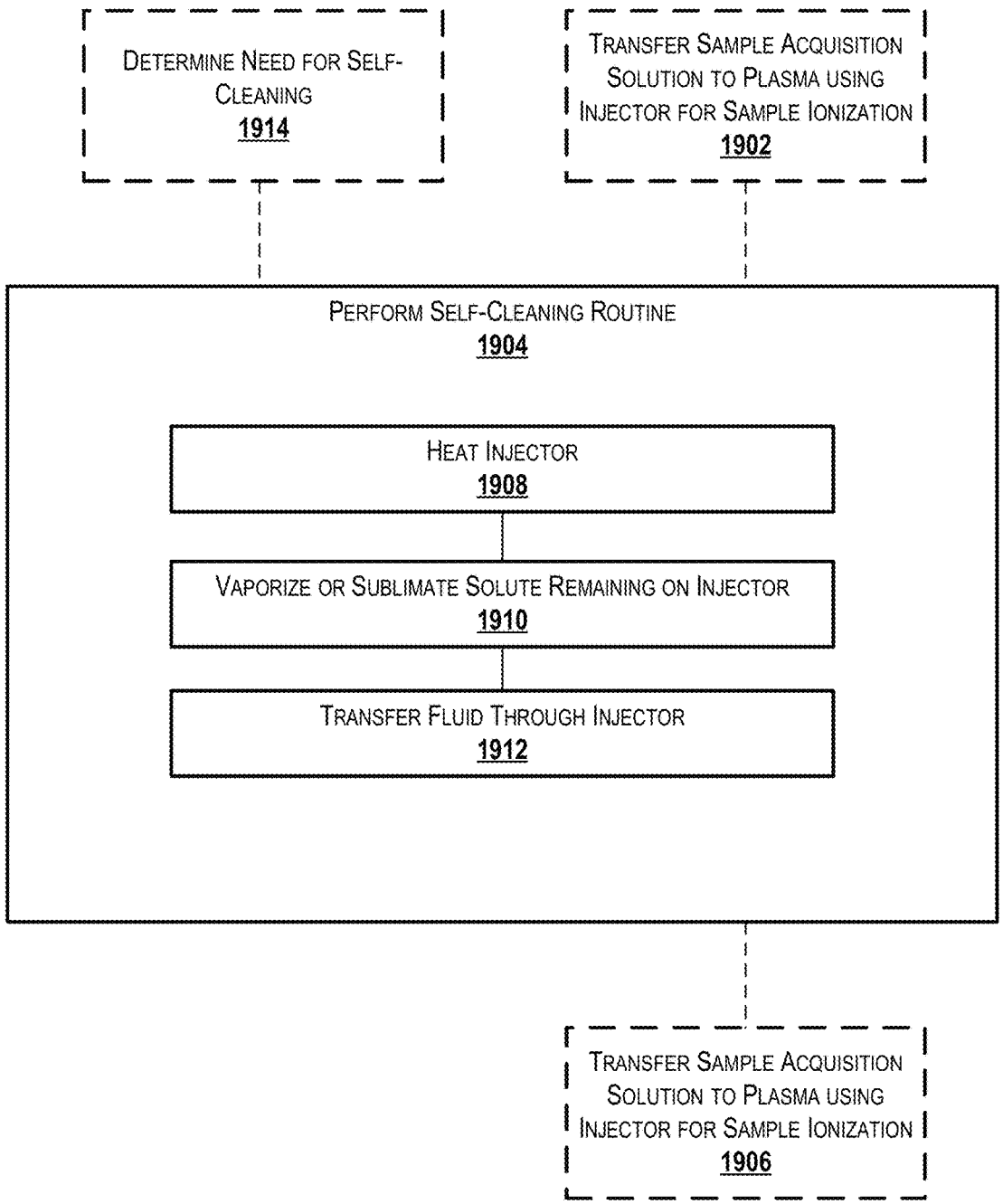
FIG. 19 is a flowchart depicting a process for self-cleaning an injector according to certain aspects of the present disclosure.

FIG. 19 is a flowchart depicting a process 1900 for self-cleaning an injector according to certain aspects of the present disclosure. Self-cleaning of an injector can be used to remove buildup from an injector of an inductively coupled plasma system, such as residue from salt of a stabilizing solution or collection of water droplets. In some cases, self-cleaning can occur before, after, or between transferring samples (e.g., cells) through the injector for ionization by the plasma of the inductively coupled plasma system.

At optional block 1902, a sample acquisition solution (e.g., a solution containing cells, and optionally a stabilizing solution) can be transferred to a plasma through an injector. During the transfer of the sample acquisition solution through the injector at block 1902, residue can build up on the injector.

At block 1904, a self-cleaning routine can be performed. In some cases, the self-cleaning routine can be performed automatically after completion of the transfer of the sample acquisition solution at block 1902, such as automatically after transferring a certain amount of sample acquisition solution, after transferring all of the sample acquisition solution, or after transferring the sample acquisition solution for a certain period of time. In some cases, the self-cleaning routine can be performed automatically before beginning transfer of the sample acquisition solution at block 1906. At optional block 1904, a sample acquisition solution (e.g., a solution containing cells, and optionally a stabilizing solution) can be transferred to a plasma through an injector. In some cases, the sample acquisition solution transferred at block 1904 includes a remainder of sample acquisition solution that was not yet transferred at block 1902.

In some cases, the self-cleaning routine performed at block 1904 can be triggered. In such cases, at optional block 1914, a need for self-cleaning can be determined, and the self-cleaning routine at block 1904 can be performed automatically in response to a determination that a need for self-cleaning exists. The need for self-cleaning can be based on a detected condition of the injector (e.g., based on a visual sensor associated with the injector) or based on an inferred condition of the injector. An inferred condition of the injector can be based on expected outcome (e.g., after a preset amount fluid has passed through the injector or after a preset amount of running time) or can be based on post-injector measurements (e.g., based on characteristic changes to expected output from an elemental detector associated with the inductively coupled plasma source). For example, a calibrated sample can be passed through the injector, be ionized, and then be analyzed by the elemental analyzer. The measurements from the elemental analyzer can be used to generate an inference that the injector is in need of self-cleaning. In other cases, as sample acquisition solution passed through the injector, ionized, and analyzed by the elemental analyzer, the measurements from the elemental analyzer may change over time in a recognizable pattern that can be used to inter that the injector is in need of self-cleaning. In some cases, the need for self-cleaning can exist when a measured or inferred amount of buildup exists in the injector at or above a threshold amount of buildup, such as based on a percent amount of cross-sectional area free from buildup as described herein.

The self-cleaning routine at block 1904 can include heating the injector at block 1908. Solute or other residue on the injector can be vaporized or sublimated at block 1910, due at least in part to the elevated temperature of the injector. At block 1912, fluid can be passed through the injector. The fluid passed through the injector at block 1912 can be sample acquisition solution (e.g., sample acquisition solution of blocks 1902 or 1906) or another fluid, such as deionized water or argon gas. In some cases, block 1912 can occur simultaneously with and/or subsequent to block 1910. In some cases, heating the injector 1908 can occur before and/or simultaneously with any of blocks 1910 and 1912.

In some cases, transferring the sample acquisition solution at block 1902 and/or block 1904 can be performed without heating the injector.

The foregoing description of the embodiments, including illustrated embodiments, has been presented only for the purpose of illustration and description and is not intended to be exhaustive or limiting to the precise forms disclosed. Numerous modifications, adaptations, and uses thereof will be apparent to those skilled in the art.

As used below, any reference to a series of examples is to be understood as a reference to each of those examples disjunctively (e.g., "Examples 1-4" is to be understood as "Examples 1, 2, 3, or 4").

Example 1 is a sample, comprising: element-tagged analyte comprising analyte bound to element-tagged affinity reagent, wherein the element-tagged affinity reagent comprises an affinity reagent for binding to the analyte and a metal-binding moiety bound to one or more metal elements; and a stabilizing solution having a total dissolved solids at or below approximately 0.2%, wherein the stabilizing solution contains a salt. In some cases, the salt of the sample of example 1 is present in concentrations of at least 5 mM.

Example 2 is the sample of example(s) 1, wherein the salt is a non-metallic salt.

Example 3 is the sample of example(s) 1 or 2, wherein the salt is devoid of carbon.

Example 4 is the sample of example(s) 1-3, wherein the salt is devoid of metals having an atomic mass unit greater than 80.

Example 5 is the sample of example(s) 1-4, wherein the salt includes nitrogen.

Example 6 is the sample of example(s) 1-5, wherein the salt is ammonium nitrate.

Example 7 is the sample of example(s) 1-6, wherein the salt has a vapor pressure of at least 3 Pa at 100° C.

Example 8 is the sample of example(s) 1-7, wherein the salt has a vapor pressure of at least 130 Pa at 150° C.

Example 9 is the sample of example(s) 1-8, wherein the salt has a vapor pressure of at least 250 Pa at 160° C.

Example 10 is the sample of example(s) 1-5 or 7-9, wherein the salt is ammonium acetate.

Example 11 is the sample of example(s) 1-10, wherein the analyte comprises whole cells.

Example 12 is the sample of example(s) 11, wherein the stabilizing solution induces sufficiently low osmotic pressure on a membrane of the analyte to avoid osmotic lysis of the analyte.

Example 13 is the sample of example(s) 1-12, wherein the salt is present in the stabilizing solution in concentrations of at or less than 25 mM.

Example 14 is the sample of example(s) 1-13, wherein the stabilizing solution has a pH of between 5-9.

Example 15 is the sample of example(s) 1-13, wherein the stabilizing solution has a pH of between 6-8.

Example 16 is the sample of example(s) 1-15, wherein the metal-binding moiety includes a polymer linked to the affinity reagent and comprising at least one metal-binding pendant group that comprises at least one metal atom.

Example 17 is the sample of example(s) 1-16, wherein the element-tagged analyte comprises first analyte tagged with a first element tag and second analyte tagged with a second element tag that is distinguishable from the first element tag through elemental analysis.

Example 18 is the sample of example(s) 1-17, wherein the affinity reagent comprises an antibody.

Example 19 is a sample-making kit, comprising element-tagged affinity reagent comprising an affinity reagent for binding to an analyte and a metal-binding moiety bound to one or more metal elements; and a stabilizing solution having a total dissolved solids at or below approximately 0.2%, wherein the stabilizing solution contains a salt. In some cases, the salt of the sample-making kit of example 19 is present in concentrations of at least 5 mM.

Example 20 is the sample-making kit of example(s) 19, wherein the salt is a non-metallic salt.

Example 21 is the sample-making kit of example(s) 19-20, wherein the salt is devoid of carbon.

Example 22 is the sample-making kit of example(s) 19-21, wherein the salt is devoid of metals having an atomic mass unit greater than 80.

Example 23 is the sample-making kit of example(s) 19-22, wherein the salt includes nitrogen.

Example 24 is the sample-making kit of example(s) 19-23, wherein the salt is ammonium nitrate.

Example 25 is the sample-making kit of example(s) 19-24, wherein the salt has a vapor pressure of at least 3 Pa at 100° C.

Example 26 is the sample-making kit of example(s) 19-25, wherein the salt has a vapor pressure of at least 130 Pa at 150° C.

Example 27 is the sample-making kit of example(s) 19-26, wherein the salt has a vapor pressure of at least 250 Pa at 160° C.

Example 28 is the sample-making kit of example(s) 19-23 or 25-27, wherein the salt is ammonium acetate.

Example 29 is the sample-making kit of example(s) 19-28, wherein the affinity reagent is bindable to surfaces of whole cells.

Example 30 is the sample-making kit of example(s) 29, wherein the stabilizing solution induces sufficiently low osmotic pressure on membranes of whole cells bound to the affinity reagent to avoid osmotic lysis of the whole cells.

Example 31 is the sample-making kit of example(s) 19-29, wherein the salt is present in the stabilizing solution in concentrations of at or less than 25 mM.

Example 32 is the method of example(s) 19-31, wherein the stabilizing solution has a pH of between 5-9.

Example 33 is the method of example(s) 19-31, wherein the stabilizing solution has a pH of between 6-8.

Example 34 is the sample-making kit of example(s) 19-33, wherein the metal-binding moiety includes a polymer linked to the affinity reagent and comprising at least one metal-binding pendant group that comprises at least one metal atom.

Example 35 is the sample-making kit of example(s) 19-34, wherein the element-tagged affinity reagent comprises first affinity reagent tagged with a first element tag and second affinity reagent tagged with a second element tag that is distinguishable from the first element tag through elemental analysis.

Example 36 is a method, comprising: receiving a sample comprising an element-tagged analyte and a stabilizing solution; transporting the sample towards a plasma of an inductively coupled plasma source in a downstream direction to ionize the sample, wherein transporting the sample comprises passing the sample past an inner wall of an injector; ionizing the sample at the plasma; and performing elemental analysis on the ionized sample to detect elements of the element-tagged analyte.

Example 37 is the method of example(s) 36, wherein the analyte comprises whole cells, and wherein transporting the sample towards the plasma comprises transporting the whole cells towards the plasma.

Example 38 is the method of example(s) 36 or 37, wherein transporting the sample towards the plasma comprises transporting the sample through an injector having an inner diameter of between approximately 0.5 mm and 5 mm.

Example 39 is the method of example(s) 36-38, wherein receiving the sample further comprises mixing the element-tagged analyte and the stabilizing solution.

Example 40 is the method of example(s) 36-39, wherein the stabilizing solution includes a salt selected to obtain a salt deposition of less than 2% of the total flow of salt material in the injector during a 48 hour sample run.

Example 41 is the method of example(s) 36-40, wherein the stabilizing solution includes a salt selected to maintain a signal drop percentage during elemental analysis of at or less than 5% during a 48 hour sample run.

Example 42 is a method, comprising providing element-tagged analyte, wherein the element-tagged analyte comprises a sample containing whole cells labeled with element-tagged affinity reagent, wherein each element-tagged affinity reagent comprises an affinity reagent bound to an analyte of the sample and a metal-binding moiety bound to one or more metal elements; and mixing the element-tagged analyte with a stabilizing solution having a total dissolved solids at or below approximately 0.2%, wherein the stabilizing solution contains a salt. In some cases, the salt of the method of example 42 is present in concentrations of at least 5 mM.

Example 43 is the method of example(s) 42, wherein the salt is a non-metallic salt.

Example 44 is the method of example(s) 42 or 43, wherein the salt is devoid of carbon.

Example 45 is the method of example(s) 42-44, wherein the salt is devoid of metals having an atomic mass unit greater than 80.

Example 46 is the method of example(s) 42-45, wherein the salt includes nitrogen.

Example 47 is the method of example(s) 42-46, wherein the salt is ammonium nitrate.

Example 48 is the method of example(s) 42-47, wherein the salt has a vapor pressure of at least 3 Pa at 100° C.

Example 49 is the method of example(s) 48, further comprising passing the sample acquisition solution through an injector heated to a temperature of at least 100° C.

Example 50 is the method of example(s) 42-49, wherein the salt has a vapor pressure of at least 130 Pa at 150° C.

Example 51 is the method of example(s) 50, further comprising passing the sample acquisition solution through an injector heated to a temperature of at least 150° C.

Example 52 is the method of example(s) 42-51, wherein the salt has a vapor pressure of at least 250 Pa at 160° C.

Example 53 is the method of example(s) 52, further comprising passing the sample acquisition solution through an injector heated to a temperature of at least 160° C.

Example 54 is the method of example(s) 42-46 or 48-53, wherein the salt is ammonium acetate.

Example 55 is the method of example(s) 42-54, wherein the affinity reagent is bindable to surfaces of the whole cells.

Example 56 is the method of example(s) 42-55, wherein the stabilizing solution induces sufficiently low osmotic pressure on membranes of whole cells bound to the affinity reagent to avoid osmotic lysis of the whole cells.

Example 57 is the method of example(s) 42-56, wherein the salt is present in the stabilizing solution in concentrations of at or less than 25 mM.

Example 58 is the method of example(s) 42-57, wherein the stabilizing solution has a pH of between 5-9.

Example 59 is the method of example(s) 42-57, wherein the stabilizing solution has a pH of between 6-8.

Example 60 is the method of example(s) 42-59, wherein the metal-binding moiety includes a polymer linked to the affinity reagent and comprising at least one metal-binding pendant group that comprises at least one metal atom.

Example 61 is the method of example(s) 42-60, wherein the element-tagged affinity reagent comprises first affinity reagent tagged with a first element tag and second affinity reagent tagged with a second element tag that is distinguishable from the first element tag through elemental analysis.

Example 62 is the method of example(s) 42-61, wherein the salt is selected to obtain a salt deposition of less than 2% during a 48 hour sample run.

Example 63 is the method of example(s) 42-62, wherein the stabilizing solution includes a salt selected to maintain a signal drop percentage during elemental analysis of at or less than 5% during a 48 hour sample run Example 64 is a stabilizing solution mixable with a sample for use in inductively coupled plasma elemental analysis, comprising: solute and solvent, wherein the solute is a salt, wherein the solution has a total dissolved solids at or below approximately 0.2%, and wherein the solution is devoid of metals having an atomic mass unit greater than 80. In some cases, the salt of the stabilizing solution of example 64 is present in concentrations of at least 5 mM.

Example 65 is the solution of example(s) 64, wherein the salt is a non-metallic salt.

Example 66 is the solution of example(s) 64 or 65, wherein the salt is devoid of carbon.

Example 67 is the solution of example(s) 64-66, wherein the salt includes nitrogen.

Example 68 is the solution of example(s) 64-67, wherein the salt is ammonium nitrate.

Example 69 is the solution of example(s) 64-68, wherein the salt has a vapor pressure of at least 3 Pa at 100° C.

Example 70 is the solution of example(s) 64-69, wherein the salt has a vapor pressure of at least 130 Pa at 150° C.

Example 71 is the solution of example(s) 64-70, wherein the salt has a vapor pressure of at least 250 Pa at 160° C.

Example 72 is the solution of example(s) 64-67 or 69-71, wherein the salt is ammonium acetate.

Example 73 is the solution of example(s) 64-72, wherein the stabilizing solution induces sufficiently low osmotic pressure on a membrane of whole cells of the sample to avoid osmotic lysis of the whole cells.

Example 74 is the solution of example(s) 64-73, wherein the salt is present in the stabilizing solution in concentrations of at or less than 25 mM.

Example 75 is the solution of example(s) 64-74, wherein the stabilizing solution has a pH of between 5-9.

Example 76 is the solution of example(s) 64-75, wherein the stabilizing solution has a pH of between 6-8.

Example 77 is an apparatus, comprising: an inductively coupled plasma source for generating a plasma; an injector having a sample inlet for receiving a sample comprising an element-tagged analyte, wherein the injector is positioned upstream of the inductively coupled plasma source to supply the sample to the plasma; and a heat source thermally coupled to the injector for heating the injector.

Example 78 is the apparatus of example(s) 77, further comprising a heat transfer device thermally coupled to the injector for conveying heat from the heat source.

Example 79 is the apparatus of example(s) 78, wherein the heat transfer device comprises a metallic jacket surrounding at least a portion of the injector.

Example 80 is the apparatus of example(s) 78 or 79, wherein the heat source includes at least a portion of a spray chamber positioned upstream of the injector such that heat from the spray chamber is transferred to the injector through the heat transfer device.

Example 81 is the apparatus of example(s) 78-80, wherein the heat source includes the plasma.

Example 82 is the apparatus of example(s) 77-81, wherein the heat source comprises an electrical resistance heat source.

Example 83 is the apparatus of example(s) 77-82, further comprising one or more heat pipes extending along a length of the injector.

Example 84 is the apparatus of example(s) 83, wherein the one or more heat pipes are arranged to conduct thermal energy from a higher temperature portion of the injector towards a lower temperature portion of the injector.

Example 85 is the apparatus of example(s) 77-84, further comprising a mass spectrometer positioned downstream of the inductively coupled plasma source for receiving ions from the inductively coupled plasma source.

Example 86 is the apparatus of example(s) 77-85, wherein the injector has an inner diameter between approximately 0.5 mm and 5 mm.

Example 87 is the apparatus of example(s) 77-86, further comprising a sample source coupled to the injector for providing the sample and a stabilization solution.

Example 88 is the apparatus of example(s) 87, wherein the heat transfer device is coupled to the injector to heat an inner surface of the injector to a temperature sufficient to vaporize or sublimate solute of the stabilization solution.

Example 89 is the apparatus of example(s) 77-88, wherein the heat transfer device is coupled to the injector to heat an inner surface of the injector to a temperature of at least 150° C.

Example 90 is a method of using the apparatus of example(s) 77-89, comprising: heating the injector using the heat source; passing a sample through the injector to the plasma; ionizing the sample; and performing elemental analysis on the ionized sample.

Example 91 is the method of example(s) 90, wherein passing the sample through the injector comprises passing a solution comprising an element-tagged analyte and a stabilizing solution.

Example 92 is the method of example(s) 91, wherein heating the injector includes heating the injector to a temperature suitable to obtain a salt deposition of less than 2% during a 48 hour sample run.

Example 93 is the method of example(s) 90-92, wherein heating the injector comprises passing electricity through an electrical resistance heat source, wherein the heat source is the electrical resistance heat source.

Example 94 is the method of example(s) 90-93, wherein heating the injector comprises conducting heat from a higher temperature portion of the injector towards a lower temperature portion of the injector using a heat transfer device.

Example 95 is the method of example(s) 90-94, wherein heating the injector comprises heating the inner wall to a temperature sufficient to vaporize or sublimate or decompose solute of the stabilizing solution.

Example 96 is a method, comprising: receiving a sample comprising an element-tagged analyte and a stabilizing solution; transporting the sample towards a plasma of an inductively coupled plasma source in a downstream direction to ionize the sample, wherein transporting the sample comprises passing the sample past an inner wall of an injector; and heating the inner wall of the injector.

Example 97 is the method of example(s) 96, wherein heating the inner wall of the injector begins prior to transporting the sample towards the plasma.

Example 98 is the method of example(s) 96, wherein heating the inner wall of the injector begins after transporting the sample towards the plasma.

Example 99 is the method of example(s) 96-98, further comprising passing the sample through a spray chamber, wherein heating the inner wall of the injector comprises conducting heat through a heat transfer device from the spray chamber.

Example 100 is the method of example(s) 96-99, wherein heating the inner wall of the injector comprises generating heat at a heat source.

Example 101 is the method of example(s) 100, wherein generating heat at the heat source comprises passing electricity through an electrical resistance heat source.

Example 102 is the method of example(s) 96-101, wherein heating the inner wall of the injector comprises conducting heat from a higher temperature portion of the injector towards a lower temperature portion of the injector using a heat transfer device.

Example 103 is the method of example(s) 96-102, wherein heating the inner wall of the injector comprises heating the inner wall to a temperature sufficient to vaporize or sublimate solute of the stabilizing solution.

Example 104 is the method of example(s) 96-103, wherein heating the inner wall of the injector comprises heating the inner wall to a temperature of at least 150° C.

Example 105 is the method of example(s) 96-104, further comprising: transporting ions of the ionized sample to a mass spectrometer; and analyzing the ions by the mass spectrometer.

Example 106 is the method of example(s) 96-105, wherein the analyte comprises whole cells, and wherein transporting the sample towards the plasma comprises transporting the whole cells towards the plasma.

Example 107 is the method of example(s) 96-106, wherein transporting the sample towards the plasma comprises transporting the sample through an injector having an inner diameter of between approximately 0.5 mm and 5 mm.

Example 108 is the method of example(s) 96-107, wherein receiving the sample further comprises mixing the element-tagged analyte and the stabilizing solution.

Example 109 is the method of example(s) 96-108, wherein heating the inner wall of the injector includes heating the inner wall to a temperature suitable to obtain a salt deposition of less than 2% during a 48 hour sample run.

Example 110 is an apparatus, comprising: an injector positionable upstream of an inductively coupled plasma source and suitable for conveying a sample to a plasma of the inductively coupled plasma source, the injector having a sample inlet for receiving the sample, wherein the sample comprise an element-tagged analyte; and a heat source thermally coupled to the injector for heating the injector.

Example 111 is the apparatus of example(s) 110, further comprising a heat transfer device thermally coupled to the injector for conveying heat from the heat source.

Example 112 is the apparatus of example(s) 111, wherein the heat transfer device comprises a metallic jacket surrounding at least a portion of the injector.

Example 113 is the apparatus of example(s) 111 or 112, wherein the heat source includes at least a portion of a spray chamber positioned upstream of the injector such that heat from the spray chamber is transferred to the injector through the heat transfer device.

Example 114 is the apparatus if claim 111-113, wherein the heat source includes the plasma.

Example 115 is the apparatus of example(s) 110-114, wherein the heat source comprises an electrical resistance heat source.

Example 116 is the apparatus of example(s) 110-115, further comprising one or more heat pipes extending along a length of the injector.

Example 117 is the apparatus of example(s) 116, wherein the one or more heat pipes are arranged to conduct thermal energy from a higher temperature portion of the injector towards a lower temperature portion of the injector.

Example 118 is the apparatus of example(s) 110-117, further comprising a mass spectrometer positionable downstream of the inductively coupled plasma source for receiving ions from the inductively coupled plasma source.

Example 119 is the apparatus of example(s) 110-118, wherein the injector has an inner diameter between approximately 0.5 mm and 5 mm.

Example 120 is the apparatus of example(s) 110-119, further comprising a sample source coupled to the injector for providing the sample and a stabilization solution.

Example 121 is the apparatus of example(s) 120, wherein the heat transfer device is coupled to the injector to heat an inner surface of the injector to a temperature sufficient to vaporize or sublimate solute of the stabilization solution.

Example 122 is the apparatus of example(s) 110-121, wherein the heat transfer device is coupled to the injector to heat an inner surface of the injector to a temperature of at least 150° C.

What is claimed is:

1. A sample-making kit, comprising element-tagged affinity reagent comprising an affinity reagent capable of specifically binding to an analyte and a metal-binding moiety bound to one or more metal elements; and
    a stabilizing solution having a total dissolved solids at or below approximately 0.2%, wherein the stabilizing solution has a pH of between 5-9 and comprises a salt, wherein:
    the salt is present in concentrations of 5 mM to 25 mM, the salt is ammonium nitrate, and
    the stabilizing solution prevents or reduces signal drop and deposition of the salt on an injector configured to convey a sample solution comprising the analyte, the element-tagged affinity reagent, and the stabilizing solution to an inductively coupled plasma.

2. The sample-making kit of claim 1, wherein the affinity reagent is bindable to surface of whole cells.

3. The sample-making kit of claim 2, wherein the stabilizing solution induces sufficiently low osmotic pressure on membranes of whole cells bound to the affinity reagent to avoid osmotic lysis of the whole cells.

4. The sample-making kit of claim 1, wherein the metal-binding moiety includes a polymer linked to the affinity reagent and comprising at least one metal-binding pendant group that comprises at least one metal atom.

5. A method, comprising
    providing an element-tagged analyte, wherein the element-tagged analyte comprises a sample containing whole cells each bound to an element-tagged affinity reagent, wherein each of the element-tagged affinity reagents comprises an affinity reagent and a metal-binding moiety wherein the affinity reagent is bound to the whole cell and the metal binding moiety is bound to one or more metal elements; and
    mixing the element-tagged analyte with a stabilizing solution having a pH of between 5-9 and having a total dissolved solids at or below approximately 0.2%, wherein:
    the stabilizing solution comprises a salt,
    the salt is present in concentrations of 5 mM to 25 mM, the salt is ammonium nitrate, and
    the stabilizing solution prevents or reduces signal drop and deposition of the salt on an injector configured to convey a sample solution comprising the analyte, the element-tagged affinity reagent, and the stabilizing solution to an inductively coupled plasma.

6. The method of claim 5, further comprising passing the stabilizing solution through the injector heated to a temperature of at least 100° C.

7. The sample-making kit of claim 1, wherein the stabilizing solution does not comprise carbon.

8. The sample-making kit of claim 1, wherein the stabilizing solution does not comprise a metal having an atomic mass unit greater than 80.

9. The sample-making kit of claim 1, wherein the element-tagged affinity reagent comprises 145Nd-CD4.

10. The sample-making kit of claim 1, wherein the salt is present in a concentration of 25 mM.

11. The sample-making kit of claim 1, wherein the stabilizing solution has the total dissolved solids at or below 0.1%.

12. The sample-making kit of claim 1, wherein the stabilizing solution further comprises one or more salts selected from the group consisting of ammonium acetate, ammonium phosphate, and ammonium formate.

13. The sample-making kit of claim 1, wherein the one or more metal elements of the element-tagged affinity reagent is selected from the group consisting of 145Nd, 146Nd, 147Sm, 155Gd, 159Tb, 160Gd, and 171Yb.

14. The sample-making kit of claim 1, wherein the affinity reagent is selected from the group consisting of an aptamer, a lectin, and a polysaccharide.

15. The sample-making kit of claim 1, wherein the metal binding moiety of the element-tagged affinity reagent is 1,4,7,10-tetraazacyclododecane-1,4,7,10-tetraacetic acid (DOTA) or diethylenetriaminepentaacetic acid (DTPA).

16. The sample-making kit of claim 1, wherein the stabilizing solution further comprises an azide-based salt.

17. The sample-making kit of claim 1, further comprising a sample, wherein the stabilizing solution is mixed with the sample.

18. The sample-making kit of claim 17, wherein the sample is a biological sample.

* * * * *